United States Patent
Hidai et al.

(10) Patent No.: US 9,738,884 B2
(45) Date of Patent: *Aug. 22, 2017

(54) THERAPEUTIC AGENT FOR EPITHELIAL AND ENDOTHELIAL INJURY

(71) Applicant: NIHON UNIVERSITY, Tokyo (JP)

(72) Inventors: Chiaki Hidai, Tokyo (JP); Hisataka Kitano, Tokyo (JP); Atsushi Mamiya, Tokyo (JP)

(73) Assignee: NIHON UNIVERSITY, Tokyo (JP)

( * ) Notice: Subject to any disclaimer, the term of this patent is extended or adjusted under 35 U.S.C. 154(b) by 255 days.

This patent is subject to a terminal disclaimer.

(21) Appl. No.: 14/396,335

(22) PCT Filed: Apr. 30, 2013

(86) PCT No.: PCT/JP2013/062989
§ 371 (c)(1),
(2) Date: Feb. 12, 2015

(87) PCT Pub. No.: WO2013/162078
PCT Pub. Date: Oct. 31, 2013

(65) Prior Publication Data
US 2015/0175995 A1    Jun. 25, 2015

(30) Foreign Application Priority Data

Apr. 27, 2012  (JP) ................. 2012-102910

(51) Int. Cl.
| | | |
|---|---|---|
| A61K 38/00 | (2006.01) | |
| C12N 9/64 | (2006.01) | |
| C07K 14/745 | (2006.01) | |
| A61K 38/48 | (2006.01) | |

(52) U.S. Cl.
CPC .......... *C12N 9/644* (2013.01); *A61K 38/4846* (2013.01); *C07K 14/745* (2013.01); *A61K 38/00* (2013.01)

(58) Field of Classification Search
CPC .................. A61K 38/4846; C12Y 304/21022
See application file for complete search history.

(56) References Cited

U.S. PATENT DOCUMENTS

| | | | |
|---|---|---|---|
| 6,315,995 B1 | 11/2001 | Pinsky et al. | |
| 6,316,403 B1 | 11/2001 | Pinsky et al. | |
| 8,716,448 B2 * | 5/2014 | Schellenberger | C12N 9/6437 530/384 |
| 9,371,523 B2 * | 6/2016 | Hidai | A61K 38/4846 |
| 2005/0048133 A1 | 3/2005 | Pinsky et al. | |
| 2005/0250688 A1 | 11/2005 | Pinsky et al. | |
| 2008/0102115 A1 * | 5/2008 | Oyhenart | C12Y 304/2102 424/457 |
| 2010/0239554 A1 | 9/2010 | Schellenberger et al. | |
| 2010/0323956 A1 | 12/2010 | Schellenberger et al. | |
| 2011/0046060 A1 | 2/2011 | Schellenberger et al. | |
| 2011/0046061 A1 | 2/2011 | Schellenberger et al. | |
| 2011/0077199 A1 | 3/2011 | Schellenberger et al. | |
| 2011/0154516 A1 | 6/2011 | Stafford et al. | |
| 2011/0172146 A1 | 7/2011 | Schellenberger et al. | |
| 2012/0263701 A1 | 10/2012 | Schellenberger et al. | |
| 2012/0263703 A1 | 10/2012 | Schellenberger et al. | |

FOREIGN PATENT DOCUMENTS

| | | |
|---|---|---|
| JP | 2001-501612 A | 2/2001 |
| WO | 2009/051717 A2 | 4/2009 |
| WO | 2009/137254 A2 | 11/2009 |
| WO | 2009/140015 A2 | 11/2009 |
| WO | 2011/028299 A1 | 3/2011 |
| WO | 2012/081711 A1 | 6/2012 |

OTHER PUBLICATIONS

Vleig et al. 2000; High levels of factor IX increase the risk of venous thrombosis. Blood 95(12): 3678-3682.*
Bernard et al. 2000; Causes of sepsis: The inflammatory cascade and hypercoagulable state. Medscape on the web at mescape.org/viewarticle/434469_3.*
Extended European Search Report issued Sep. 8, 2105, in European Patent Application No. 13782578.2.
Atoda et al., "Characterization of a Monoclonal Antibody B1 that Recognizes Phosphorylated Ser-158 in the Activation Peptide Region of Human Coagulation Factor IX," The Journal of Biological Chemistry (Apr. 7, 2006), vol. 281, No. 14, pp. 9314-9320.
English translation of International Preliminary Report on Patentability and Written Opinion issued Jul. 14, 2014, in PCT International Application No. PCT/JP2013/062989.
English translation of International Search Report issued Jul. 9, 2013, in PCT International Application No. PCT/JP2013/062989.
Guyton, Arthur C. and John E. Hall (2000). Textbook of Medical Physiology, 10th ed. Philadelphia: W. B. Saunders Company. Chapter 36, Hemostasis and Blood Coagulation, pp. 419-429.
Harrison's Principles of Internal Medicine, 18th ed. (2012). Chapter 271, Severe Sepsis and Shock, pp. 2223-2232.
European Office Action, dated Apr. 11, 2017, for European Application No. 13782578.2.

* cited by examiner

*Primary Examiner* — Karen Cochrane Carlson
(74) *Attorney, Agent, or Firm* — Birch, Stewart, Kolasch & Birch, LLP

(57) ABSTRACT

The present invention provides a therapeutic agent for epithelial and endothelial injury, and in particular, for epithelial and endothelial microinjury, and the like. The therapeutic agent according to the present invention comprises, for example, a peptide of the following (a), (b), etc., a derivative thereof, or their salt: (a) a peptide comprising the amino acid sequence shown in any one of SEQ ID NOS: 10, 4, 12 and 6; or (b) a peptide comprising the amino acid sequence shown in any one of SEQ ID NOS: 16, 18, 20 and 22.

9 Claims, 10 Drawing Sheets
(6 of 10 Drawing Sheet(s) Filed in Color)

control 47-471 control 192-216

SEQUENCE LISTING

<160> NUMBER OF SEQ ID NOS: 26

<210> SEQ ID NO 1
<211> LENGTH: 1278
<212> TYPE: DNA
<213> ORGANISM: Mus musculus
<220> FEATURE:
<221> NAME/KEY: CDS
<222> LOCATION: (1)..(1278)

<400> SEQUENCE: 1

```
tat aat tca gga aaa cta gaa gag ttt gtt cga gga aac ctt gaa aga      48
Tyr Asn Ser Gly Lys Leu Glu Glu Phe Val Arg Gly Asn Leu Glu Arg
1               5                  10                  15 gag tgt ata gaa gaa aga tgt agt ttt gaa gaa gca cga gaa gtt ttt      96
Glu Cys Ile Glu Glu Arg Cys Ser Phe Glu Glu Ala Arg Glu Val Phe
                20                  25                  30 gaa aac act gaa aaa act act gaa ttt tgg aag cag tat gtt gat gga     144
Glu Asn Thr Glu Lys Thr Thr Glu Phe Trp Lys Gln Tyr Val Asp Gly
            35                  40                  45 gat cag tgt gaa tca aat cct tgt tta aat ggt gga ata tgc aag gat     192
Asp Gln Cys Glu Ser Asn Pro Cys Leu Asn Gly Gly Ile Cys Lys Asp
        50                  55                  60 gat att agt tcc tat gaa tgc tgg tgc caa gtt gga ttt gaa gga agg     240
Asp Ile Ser Ser Tyr Glu Cys Trp Cys Gln Val Gly Phe Glu Gly Arg
65                  70                  75                  80 aac tgt gaa tta gat gca acg tgt aac att aaa aat ggc agg tgc aag     288
Asn Cys Glu Leu Asp Ala Thr Cys Asn Ile Lys Asn Gly Arg Cys Lys
                85                  90                  95 cag ttt tgt aaa aac agt cct gat aac aag gta att tgt tcc tgc act     336
Gln Phe Cys Lys Asn Ser Pro Asp Asn Lys Val Ile Cys Ser Cys Thr
                100                 105                 110 gag gga tac caa ctt gca gaa gac cag aag tcc tgt gaa cca aca gtt     384
Glu Gly Tyr Gln Leu Ala Glu Asp Gln Lys Ser Cys Glu Pro Thr Val
            115                 120                 125 cca ttt cca tgt ggg aga gct tct att tca tac agt tct aaa aag atc     432
Pro Phe Pro Cys Gly Arg Ala Ser Ile Ser Tyr Ser Ser Lys Lys Ile
        130                 135                 140 acg aga gct gag act gtt ttc tct aat atg gac tat gaa aat tct act     480
Thr Arg Ala Glu Thr Val Phe Ser Asn Met Asp Tyr Glu Asn Ser Thr
145                 150                 155                 160 gaa gct gta ttc att caa gat gac atc act gat ggt gcc att ctt aat     528
Glu Ala Val Phe Ile Gln Asp Asp Ile Thr Asp Gly Ala Ile Leu Asn
                165                 170                 175 aac gtc act gaa agt agt gaa tca ctt aat gac ttc act cga gtt gtt     576
Asn Val Thr Glu Ser Ser Glu Ser Leu Asn Asp Phe Thr Arg Val Val
                180                 185                 190 ggt gga gaa aac gca aaa ccg ggt caa atc cct tgg cag gtc att tta     624
Gly Gly Glu Asn Ala Lys Pro Gly Gln Ile Pro Trp Gln Val Ile Leu
            195                 200                 205 aat ggt gaa att gag gca ttc tgt gga ggt gcc atc att aat gaa aaa     672
Asn Gly Glu Ile Glu Ala Phe Cys Gly Gly Ala Ile Ile Asn Glu Lys
        210                 215                 220 tgg att gta act gct gcc cac tgt ctt aaa cct ggt gat aaa att gag     720
Trp Ile Val Thr Ala Ala His Cys Leu Lys Pro Gly Asp Lys Ile Glu
225                 230                 235                 240 gtt gtt gct ggt gaa tat aac att gat aag aag gaa gac aca gaa caa     768
Val Val Ala Gly Glu Tyr Asn Ile Asp Lys Lys Glu Asp Thr Glu Gln
                245                 250                 255 agg aga aat gtg att cga act atc cct cat cac cag tac aat gca act     816
Arg Arg Asn Val Ile Arg Thr Ile Pro His His Gln Tyr Asn Ala Thr
```

```
                    260                 265                 270
att aat aag tat agt cat gac att gcc ttg ctg gaa ctg gat aaa cct        864
Ile Asn Lys Tyr Ser His Asp Ile Ala Leu Leu Glu Leu Asp Lys Pro
            275                 280                 285 tta ata cta aac agc tat gta aca cct atc tgt gtt gcc aat agg gaa        912
Leu Ile Leu Asn Ser Tyr Val Thr Pro Ile Cys Val Ala Asn Arg Glu
        290                 295                 300 tat aca aat atc ttc ctc aag ttt ggt tct ggc tat gtc agt ggc tgg        960
Tyr Thr Asn Ile Phe Leu Lys Phe Gly Ser Gly Tyr Val Ser Gly Trp
305                 310                 315                 320 gga aaa gtc ttc aac aaa ggg aga cag gct tcc att ctt cag tac ctt       1008
Gly Lys Val Phe Asn Lys Gly Arg Gln Ala Ser Ile Leu Gln Tyr Leu
                325                 330                 335 aga gtt cca ctg gtg gat aga gcc aca tgc ctt agg tcc aca aca ttc       1056
Arg Val Pro Leu Val Asp Arg Ala Thr Cys Leu Arg Ser Thr Thr Phe
            340                 345                 350 act atc tat aac aac atg ttc tgt gca ggc tac cgt gaa gga ggc aaa       1104
Thr Ile Tyr Asn Asn Met Phe Cys Ala Gly Tyr Arg Glu Gly Gly Lys
        355                 360                 365 gat tcg tgt gaa gga gat agt ggg gga ccc cat gtt act gaa gta gaa       1152
Asp Ser Cys Glu Gly Asp Ser Gly Gly Pro His Val Thr Glu Val Glu
370                 375                 380 ggg aca agt ttc tta act ggc att att agc tgg ggt gaa gaa tgt gca       1200
Gly Thr Ser Phe Leu Thr Gly Ile Ile Ser Trp Gly Glu Glu Cys Ala
385                 390                 395                 400 atg aaa ggc aaa tat gga ata tat act aag gtt tcc cgg tac gtc aac       1248
Met Lys Gly Lys Tyr Gly Ile Tyr Thr Lys Val Ser Arg Tyr Val Asn
                405                 410                 415 tgg att aag gaa aaa aca aag cta act taa                               1278
Trp Ile Lys Glu Lys Thr Lys Leu Thr
            420                 425

<210> SEQ ID NO 2
<211> LENGTH: 425
<212> TYPE: PRT
<213> ORGANISM: Mus musculus

<400> SEQUENCE: 2

Tyr Asn Ser Gly Lys Leu Glu Glu Phe Val Arg Gly Asn Leu Glu Arg
1               5                   10                  15

Glu Cys Ile Glu Glu Arg Cys Ser Phe Glu Glu Ala Arg Glu Val Phe
            20                  25                  30

Glu Asn Thr Glu Lys Thr Thr Glu Phe Trp Lys Gln Tyr Val Asp Gly
        35                  40                  45

Asp Gln Cys Glu Ser Asn Pro Cys Leu Asn Gly Gly Ile Cys Lys Asp
    50                  55                  60

Asp Ile Ser Ser Tyr Glu Cys Trp Cys Gln Val Gly Phe Glu Gly Arg
65                  70                  75                  80

Asn Cys Glu Leu Asp Ala Thr Cys Asn Ile Lys Asn Gly Arg Cys Lys
                85                  90                  95

Gln Phe Cys Lys Asn Ser Pro Asp Asn Lys Val Ile Cys Ser Cys Thr
            100                 105                 110

Glu Gly Tyr Gln Leu Ala Glu Asp Gln Lys Ser Cys Glu Pro Thr Val
        115                 120                 125

Pro Phe Pro Cys Gly Arg Ala Ser Ile Ser Tyr Ser Ser Lys Lys Ile
    130                 135                 140

Thr Arg Ala Glu Thr Val Phe Ser Asn Met Asp Tyr Glu Asn Ser Thr
145                 150                 155                 160
```

Glu Ala Val Phe Ile Gln Asp Asp Ile Thr Asp Gly Ala Ile Leu Asn
            165                 170                 175

Asn Val Thr Glu Ser Ser Glu Ser Leu Asn Asp Phe Thr Arg Val Val
        180                 185                 190

Gly Gly Glu Asn Ala Lys Pro Gly Gln Ile Pro Trp Gln Val Ile Leu
        195                 200                 205

Asn Gly Glu Ile Glu Ala Phe Cys Gly Gly Ala Ile Ile Asn Glu Lys
210                 215                 220

Trp Ile Val Thr Ala Ala His Cys Leu Lys Pro Gly Asp Lys Ile Glu
225                 230                 235                 240

Val Val Ala Gly Glu Tyr Asn Ile Asp Lys Lys Glu Asp Thr Glu Gln
                245                 250                 255

Arg Arg Asn Val Ile Arg Thr Ile Pro His His Gln Tyr Asn Ala Thr
                260                 265                 270

Ile Asn Lys Tyr Ser His Asp Ile Ala Leu Leu Glu Leu Asp Lys Pro
            275                 280                 285

Leu Ile Leu Asn Ser Tyr Val Thr Pro Ile Cys Val Ala Asn Arg Glu
290                 295                 300

Tyr Thr Asn Ile Phe Leu Lys Phe Gly Ser Gly Tyr Val Ser Gly Trp
305                 310                 315                 320

Gly Lys Val Phe Asn Lys Gly Arg Gln Ala Ser Ile Leu Gln Tyr Leu
                325                 330                 335

Arg Val Pro Leu Val Asp Arg Ala Thr Cys Leu Arg Ser Thr Thr Phe
                340                 345                 350

Thr Ile Tyr Asn Asn Met Phe Cys Ala Gly Tyr Arg Glu Gly Gly Lys
            355                 360                 365

Asp Ser Cys Glu Gly Asp Ser Gly Gly Pro His Val Thr Glu Val Glu
        370                 375                 380

Gly Thr Ser Phe Leu Thr Gly Ile Ile Ser Trp Gly Glu Glu Cys Ala
385                 390                 395                 400

Met Lys Gly Lys Tyr Gly Ile Tyr Thr Lys Val Ser Arg Tyr Val Asn
                405                 410                 415

Trp Ile Lys Glu Lys Thr Lys Leu Thr
            420                 425

<210> SEQ ID NO 3
<211> LENGTH: 75
<212> TYPE: DNA
<213> ORGANISM: Mus musculus
<220> FEATURE:
<221> NAME/KEY: CDS
<222> LOCATION: (1)..(75)

<400> SEQUENCE: 3 aga gct gag act gtt ttc tct aat atg gac tat gaa aat tct act gaa    48
Arg Ala Glu Thr Val Phe Ser Asn Met Asp Tyr Glu Asn Ser Thr Glu
1               5                   10                  15 gct gta ttc att caa gat gac atc act                                75
Ala Val Phe Ile Gln Asp Asp Ile Thr
            20                  25

<210> SEQ ID NO 4
<211> LENGTH: 25
<212> TYPE: PRT
<213> ORGANISM: Mus musculus

<400> SEQUENCE: 4

```
Arg Ala Glu Thr Val Phe Ser Asn Met Asp Tyr Glu Asn Ser Thr Glu
1               5                   10                  15

Ala Val Phe Ile Gln Asp Asp Ile Thr
            20                  25
```

<210> SEQ ID NO 5
<211> LENGTH: 135
<212> TYPE: DNA
<213> ORGANISM: Mus musculus
<220> FEATURE:
<221> NAME/KEY: CDS
<222> LOCATION: (1)..(135)

<400> SEQUENCE: 5

```
aga gct gag act gtt ttc tct aat atg gac tat gaa aat tct act gaa      48
Arg Ala Glu Thr Val Phe Ser Asn Met Asp Tyr Glu Asn Ser Thr Glu
1               5                   10                  15 gct gta ttc att caa gat gac atc act gat ggt gcc att ctt aat aac      96
Ala Val Phe Ile Gln Asp Asp Ile Thr Asp Gly Ala Ile Leu Asn Asn
            20                  25                  30 gtc act gaa agt agt gaa tca ctt aat gac ttc act cga                 135
Val Thr Glu Ser Ser Glu Ser Leu Asn Asp Phe Thr Arg
        35                  40                  45
```

<210> SEQ ID NO 6
<211> LENGTH: 45
<212> TYPE: PRT
<213> ORGANISM: Mus musculus

<400> SEQUENCE: 6

```
Arg Ala Glu Thr Val Phe Ser Asn Met Asp Tyr Glu Asn Ser Thr Glu
1               5                   10                  15

Ala Val Phe Ile Gln Asp Asp Ile Thr Asp Gly Ala Ile Leu Asn Asn
            20                  25                  30

Val Thr Glu Ser Ser Glu Ser Leu Asn Asp Phe Thr Arg
        35                  40                  45
```

<210> SEQ ID NO 7
<211> LENGTH: 2735
<212> TYPE: DNA
<213> ORGANISM: Mus musculus
<220> FEATURE:
<221> NAME/KEY: CDS
<222> LOCATION: (2)..(1417)

<400> SEQUENCE: 7

```
g atg aag cac ctg aac acc gtc atg gca gaa tcc ccg gct ctc atc acc    49
  Met Lys His Leu Asn Thr Val Met Ala Glu Ser Pro Ala Leu Ile Thr
  1               5                   10                  15 atc ttc ctt tta gga tat cta ctc agt acc gaa tgt gca gtt ttc ctt     97
Ile Phe Leu Leu Gly Tyr Leu Leu Ser Thr Glu Cys Ala Val Phe Leu
            20                  25                  30 gat cgt gaa aat gcc acc aaa att ctt acc cgt cca aag aga tat aat    145
Asp Arg Glu Asn Ala Thr Lys Ile Leu Thr Arg Pro Lys Arg Tyr Asn
        35                  40                  45 tca gga aaa cta gaa gag ttt gtt cga gga aac ctt gaa aga gag tgt    193
Ser Gly Lys Leu Glu Glu Phe Val Arg Gly Asn Leu Glu Arg Glu Cys
    50                  55                  60 ata gaa gaa aga tgt agt ttt gaa gaa gca cga gaa gtt ttt gaa aac    241
Ile Glu Glu Arg Cys Ser Phe Glu Glu Ala Arg Glu Val Phe Glu Asn
65                  70                  75                  80 act gaa aaa act act gaa ttt tgg aag cag tat gtt gat gga gat cag    289
Thr Glu Lys Thr Thr Glu Phe Trp Lys Gln Tyr Val Asp Gly Asp Gln
```

| | | | | | | | | | | | | | | | | |
|---|---|---|---|---|---|---|---|---|---|---|---|---|---|---|---|---|
| | | 85 | | | | | 90 | | | | | 95 | | | | |
| tgt | gaa | tca | aat | cct | tgt | tta | aat | ggt | gga | ata | tgc | aag | gat | gat | att | 337 |
| Cys | Glu | Ser | Asn | Pro | Cys | Leu | Asn | Gly | Gly | Ile | Cys | Lys | Asp | Asp | Ile | |
| | | 100 | | | | | 105 | | | | | 110 | | | | |
| agt | tcc | tat | gaa | tgc | tgg | tgc | caa | gtt | gga | ttt | gaa | gga | agg | aac | tgt | 385 |
| Ser | Ser | Tyr | Glu | Cys | Trp | Cys | Gln | Val | Gly | Phe | Glu | Gly | Arg | Asn | Cys | |
| | | | 115 | | | | | 120 | | | | | 125 | | | |
| gaa | tta | gat | gca | acg | tgt | aac | att | aaa | aat | ggc | agg | tgc | aag | cag | ttt | 433 |
| Glu | Leu | Asp | Ala | Thr | Cys | Asn | Ile | Lys | Asn | Gly | Arg | Cys | Lys | Gln | Phe | |
| | 130 | | | | | 135 | | | | | 140 | | | | | |
| tgt | aaa | aac | agt | cct | gat | aac | aag | gta | att | tgt | tcc | tgc | act | gag | gga | 481 |
| Cys | Lys | Asn | Ser | Pro | Asp | Asn | Lys | Val | Ile | Cys | Ser | Cys | Thr | Glu | Gly | |
| 145 | | | | | 150 | | | | | 155 | | | | | 160 | |
| tac | caa | ctt | gca | gaa | gac | cag | aag | tcc | tgt | gaa | cca | aca | gtt | cca | ttt | 529 |
| Tyr | Gln | Leu | Ala | Glu | Asp | Gln | Lys | Ser | Cys | Glu | Pro | Thr | Val | Pro | Phe | |
| | | | | 165 | | | | | 170 | | | | | 175 | | |
| cca | tgt | ggg | aga | gct | tct | att | tca | tac | agt | tct | aaa | aag | atc | acg | aga | 577 |
| Pro | Cys | Gly | Arg | Ala | Ser | Ile | Ser | Tyr | Ser | Ser | Lys | Lys | Ile | Thr | Arg | |
| | | | 180 | | | | | 185 | | | | | 190 | | | |
| gct | gag | act | gtt | ttc | tct | aat | atg | gac | tat | gaa | aat | tct | act | gaa | gct | 625 |
| Ala | Glu | Thr | Val | Phe | Ser | Asn | Met | Asp | Tyr | Glu | Asn | Ser | Thr | Glu | Ala | |
| | 195 | | | | | 200 | | | | | 205 | | | | | |
| gta | ttc | att | caa | gat | gac | atc | act | gat | ggt | gcc | att | ctt | aat | aac | gtc | 673 |
| Val | Phe | Ile | Gln | Asp | Asp | Ile | Thr | Asp | Gly | Ala | Ile | Leu | Asn | Asn | Val | |
| 210 | | | | | 215 | | | | | 220 | | | | | | |
| act | gaa | agt | agt | gaa | tca | ctt | aat | gac | ttc | act | cga | gtt | gtt | ggt | gga | 721 |
| Thr | Glu | Ser | Ser | Glu | Ser | Leu | Asn | Asp | Phe | Thr | Arg | Val | Val | Gly | Gly | |
| 225 | | | | | 230 | | | | | 235 | | | | | 240 | |
| gaa | aac | gca | aaa | ccg | ggt | caa | atc | cct | tgg | cag | gtc | att | tta | aat | ggt | 769 |
| Glu | Asn | Ala | Lys | Pro | Gly | Gln | Ile | Pro | Trp | Gln | Val | Ile | Leu | Asn | Gly | |
| | | | | 245 | | | | | 250 | | | | | 255 | | |
| gaa | att | gag | gca | ttc | tgt | gga | ggt | gcc | atc | att | aat | gaa | aaa | tgg | att | 817 |
| Glu | Ile | Glu | Ala | Phe | Cys | Gly | Gly | Ala | Ile | Ile | Asn | Glu | Lys | Trp | Ile | |
| | | | 260 | | | | | 265 | | | | | 270 | | | |
| gta | act | gct | gcc | cac | tgt | ctt | aaa | cct | ggt | gat | aaa | att | gag | gtt | gtt | 865 |
| Val | Thr | Ala | Ala | His | Cys | Leu | Lys | Pro | Gly | Asp | Lys | Ile | Glu | Val | Val | |
| | 275 | | | | | 280 | | | | | 285 | | | | | |
| gct | ggt | gaa | tat | aac | att | gat | aag | aag | gaa | gac | aca | gaa | caa | agg | aga | 913 |
| Ala | Gly | Glu | Tyr | Asn | Ile | Asp | Lys | Lys | Glu | Asp | Thr | Glu | Gln | Arg | Arg | |
| 290 | | | | | 295 | | | | | 300 | | | | | | |
| aat | gtg | att | cga | act | atc | cct | cat | cac | cag | tac | aat | gca | act | att | aat | 961 |
| Asn | Val | Ile | Arg | Thr | Ile | Pro | His | His | Gln | Tyr | Asn | Ala | Thr | Ile | Asn | |
| 305 | | | | | 310 | | | | | 315 | | | | | 320 | |
| aag | tat | agt | cat | gac | att | gcc | ttg | ctg | gaa | ctg | gat | aaa | cct | tta | ata | 1009 |
| Lys | Tyr | Ser | His | Asp | Ile | Ala | Leu | Leu | Glu | Leu | Asp | Lys | Pro | Leu | Ile | |
| | | | | 325 | | | | | 330 | | | | | 335 | | |
| cta | aac | agc | tat | gta | aca | cct | atc | tgt | gtt | gcc | aat | agg | gaa | tat | aca | 1057 |
| Leu | Asn | Ser | Tyr | Val | Thr | Pro | Ile | Cys | Val | Ala | Asn | Arg | Glu | Tyr | Thr | |
| | | | 340 | | | | | 345 | | | | | 350 | | | |
| aat | atc | ttc | ctc | aag | ttt | ggt | tct | ggc | tat | gtc | agt | ggc | tgg | gga | aaa | 1105 |
| Asn | Ile | Phe | Leu | Lys | Phe | Gly | Ser | Gly | Tyr | Val | Ser | Gly | Trp | Gly | Lys | |
| | 355 | | | | | 360 | | | | | 365 | | | | | |
| gtc | ttc | aac | aaa | ggg | aga | cag | gct | tcc | att | ctt | cag | tac | ctt | aga | gtt | 1153 |
| Val | Phe | Asn | Lys | Gly | Arg | Gln | Ala | Ser | Ile | Leu | Gln | Tyr | Leu | Arg | Val | |
| 370 | | | | | 375 | | | | | 380 | | | | | | |
| cca | ctg | gtg | gat | aga | gcc | aca | tgc | ctt | agg | tcc | aca | aca | ttc | act | atc | 1201 |
| Pro | Leu | Val | Asp | Arg | Ala | Thr | Cys | Leu | Arg | Ser | Thr | Thr | Phe | Thr | Ile | |
| 385 | | | | | 390 | | | | | 395 | | | | | 400 | |
| tat | aac | aac | atg | ttc | tgt | gca | ggc | tac | cgt | gaa | gga | ggc | aaa | gat | tcg | 1249 |

```
                Tyr Asn Asn Met Phe Cys Ala Gly Tyr Arg Glu Gly Gly Lys Asp Ser
                                405                 410                 415 tgt gaa gga gat agt ggg gga ccc cat gtt act gaa gta gaa ggg aca                1297
Cys Glu Gly Asp Ser Gly Gly Pro His Val Thr Glu Val Glu Gly Thr
            420                 425                 430 agt ttc tta act ggc att att agc tgg ggt gaa gaa tgt gca atg aaa                1345
Ser Phe Leu Thr Gly Ile Ile Ser Trp Gly Glu Glu Cys Ala Met Lys
        435                 440                 445 ggc aaa tat gga ata tat act aag gtt tcc cgg tac gtc aac tgg att                1393
Gly Lys Tyr Gly Ile Tyr Thr Lys Val Ser Arg Tyr Val Asn Trp Ile
    450                 455                 460 aag gaa aaa aca aag cta act taa tgaaaaacct atttccaaag acaattcagt               1447
Lys Glu Lys Thr Lys Leu Thr
465                 470 ggaattgaaa atgggtgatg cccttacag actagtcttt ctaccttttg ttaaatttaa               1507
atatataagt tctacaaaca ctgattttc tctgtgcata agacaagccc atctaggatc               1567
tatattgttc tagagtaagt aggttagcaa atataatcac tagagaaata gtttagtaag              1627
agattcacca tttctgtaag tccagcccct gttaaaatta gaaagtaaag ctttccgtgt              1687
tgcccataag gcgtgatggt tcttgataca gagatgtacc caattctccc tccttggcag              1747
caattcatgt tttagctctt ccttgctact ctcaattttta ttagttttct atccagaatc             1807
tttaacccat ttatggccag aagaatacaa gagcagctga aaaattaaaa ctcatcaaaa              1867
gcatgacttc ctctcctgat ttttctgaat cttgtatctt ttacaactcc caaccacaa               1927 atcactgacc tctccgtcat tctcaccttc cctttctcca tcaccactga aggaggaagc              1987
tatatgagtt ccaggacagc ctaggtacac agagaaaccc ggtcttgaaa gaaaagagag              2047
agtggggaga gagagagaga gagagagaga gagagagagg agaaagaaat gattaattta              2107
atcatattgg taatatatat atattatatc tctaaaaaaa agtcactaaa ccttacttgt              2167
aacaactgcc tatttctatg gtgtaaatat ccttactttg gtagatttca agctattaac              2227
atgaagttac tggaaaagga gttgagaaaa catatgaaa attactctta aaactgtttc               2287
aggcagtttt taacctagaa gcagctgaac tttctaggaa tacttcaaca gtgcatcttc              2347
agccttctcc agttccaacc tacctaaggg tcatgtctct cacagcaggc tcaaggctgc              2407
aagagtcatt gcaaatggcc aactgacttg cccatttatg gttttcttct caccggtaaa              2467
ctgttattgt aattaacact gtcatattga attttctaga gggatgctga ccatccgacc              2527
catttctcat ctgagacttg gtgaactggc attttaatac ttatctggac ctttgtagtg              2587
atgcataatt ggtttgaacc ccttgtcact gccacctgcc cccaccaaca caaaatccta              2647
cttcattact gctgactctg ctaacgttcc actacttgtt gcctcttttg tcttgcaaga              2707
agtatcaata aacatctttc cagatttc                                                 2735

<210> SEQ ID NO 8
<211> LENGTH: 471
<212> TYPE: PRT
<213> ORGANISM: Mus musculus

<400> SEQUENCE: 8

Met Lys His Leu Asn Thr Val Met Ala Glu Ser Pro Ala Leu Ile Thr
1               5                   10                  15

Ile Phe Leu Leu Gly Tyr Leu Leu Ser Thr Glu Cys Ala Val Phe Leu
            20                  25                  30

Asp Arg Glu Asn Ala Thr Lys Ile Leu Thr Arg Pro Lys Arg Tyr Asn
        35                  40                  45
```

```
Ser Gly Lys Leu Glu Glu Phe Val Arg Gly Asn Leu Glu Arg Glu Cys
    50                  55                  60

Ile Glu Glu Arg Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ile Cys Lys Asp Asp Ile
                100                 105                 110

Ser Ser Tyr Glu Cys Trp Cys Gln Val Gly Phe Glu Gly Arg Asn Cys
        115                 120                 125

Glu Leu Asp Ala Thr Cys Asn Ile Lys Asn Gly Arg Cys Lys Gln Phe
    130                 135                 140

Cys Lys Asn Ser Pro Asp Asn Lys Val Ile Cys Ser Cys Thr Glu Gly
145                 150                 155                 160

Tyr Gln Leu Ala Glu Asp Gln Lys Ser Cys Glu Pro Thr Val Pro Phe
                165                 170                 175

Pro Cys Gly Arg Ala Ser Ile Ser Tyr Ser Ser Lys Lys Ile Thr Arg
                180                 185                 190

Ala Glu Thr Val Phe Ser Asn Met Asp Tyr Glu Asn Ser Thr Glu Ala
            195                 200                 205

Val Phe Ile Gln Asp Asp Ile Thr Asp Gly Ala Ile Leu Asn Asn Val
    210                 215                 220

Thr Glu Ser Ser Glu Ser Leu Asn Asp Phe Thr Arg Val Val Gly Gly
225                 230                 235                 240

Glu Asn Ala Lys Pro Gly Gln Ile Pro Trp Gln Val Ile Leu Asn Gly
                245                 250                 255

Glu Ile Glu Ala Phe Cys Gly Gly Ala Ile Ile Asn Glu Lys Trp Ile
            260                 265                 270

Val Thr Ala Ala His Cys Leu Lys Pro Gly Asp Lys Ile Glu Val Val
    275                 280                 285

Ala Gly Glu Tyr Asn Ile Asp Lys Lys Glu Asp Thr Glu Gln Arg Arg
    290                 295                 300

Asn Val Ile Arg Thr Ile Pro His His Gln Tyr Asn Ala Thr Ile Asn
305                 310                 315                 320

Lys Tyr Ser His Asp Ile Ala Leu Leu Glu Leu Asp Lys Pro Leu Ile
                325                 330                 335

Leu Asn Ser Tyr Val Thr Pro Ile Cys Val Ala Asn Arg Glu Tyr Thr
            340                 345                 350

Asn Ile Phe Leu Lys Phe Gly Ser Gly Tyr Val Ser Gly Trp Gly Lys
    355                 360                 365

Val Phe Asn Lys Gly Arg Gln Ala Ser Ile Leu Gln Tyr Leu Arg Val
    370                 375                 380

Pro Leu Val Asp Arg Ala Thr Cys Leu Arg Ser Thr Thr Phe Thr Ile
385                 390                 395                 400

Tyr Asn Asn Met Phe Cys Ala Gly Tyr Arg Glu Gly Gly Lys Asp Ser
                405                 410                 415

Cys Glu Gly Asp Ser Gly Gly Pro His Val Thr Glu Val Glu Gly Thr
                420                 425                 430

Ser Phe Leu Thr Gly Ile Ile Ser Trp Gly Glu Glu Cys Ala Met Lys
            435                 440                 445

Gly Lys Tyr Gly Ile Tyr Thr Lys Val Ser Arg Tyr Val Asn Trp Ile
    450                 455                 460
```

```
Lys Glu Lys Thr Lys Leu Thr
465                 470
```

<210> SEQ ID NO 9
<211> LENGTH: 72
<212> TYPE: DNA
<213> ORGANISM: Mus musculus
<220> FEATURE:
<221> NAME/KEY: CDS
<222> LOCATION: (1)..(72)

<400> SEQUENCE: 9

```
gct gag act gtt ttc tct aat atg gac tat gaa aat tct act gaa gct    48
Ala Glu Thr Val Phe Ser Asn Met Asp Tyr Glu Asn Ser Thr Glu Ala
1               5                   10                  15 gta ttc att caa gat gac atc act                                    72
Val Phe Ile Gln Asp Asp Ile Thr
            20
```

<210> SEQ ID NO 10
<211> LENGTH: 24
<212> TYPE: PRT
<213> ORGANISM: Mus musculus

<400> SEQUENCE: 10

```
Ala Glu Thr Val Phe Ser Asn Met Asp Tyr Glu Asn Ser Thr Glu Ala
1               5                   10                  15

Val Phe Ile Gln Asp Asp Ile Thr
            20
```

<210> SEQ ID NO 11
<211> LENGTH: 132
<212> TYPE: DNA
<213> ORGANISM: Mus musculus
<220> FEATURE:
<221> NAME/KEY: CDS
<222> LOCATION: (1)..(132)

<400> SEQUENCE: 11

```
gct gag act gtt ttc tct aat atg gac tat gaa aat tct act gaa gct    48
Ala Glu Thr Val Phe Ser Asn Met Asp Tyr Glu Asn Ser Thr Glu Ala
1               5                   10                  15 gta ttc att caa gat gac atc act gat ggt gcc att ctt aat aac gtc    96
Val Phe Ile Gln Asp Asp Ile Thr Asp Gly Ala Ile Leu Asn Asn Val
            20                  25                  30 act gaa agt agt gaa tca ctt aat gac ttc act cga                    132
Thr Glu Ser Ser Glu Ser Leu Asn Asp Phe Thr Arg
        35                  40
```

<210> SEQ ID NO 12
<211> LENGTH: 44
<212> TYPE: PRT
<213> ORGANISM: Mus musculus

<400> SEQUENCE: 12

```
Ala Glu Thr Val Phe Ser Asn Met Asp Tyr Glu Asn Ser Thr Glu Ala
1               5                   10                  15

Val Phe Ile Gln Asp Asp Ile Thr Asp Gly Ala Ile Leu Asn Asn Val
            20                  25                  30

Thr Glu Ser Ser Glu Ser Leu Asn Asp Phe Thr Arg
        35                  40
```

<210> SEQ ID NO 13
<211> LENGTH: 1554

```
<212> TYPE: DNA
<213> ORGANIsM: Homo sapiens
<220> FEATURE:
<221> NAME/KEY: CDS
<222> LOCATION: (1)..(1554)

<400> SEQUENCE: 13 aca gtt ttt ctt gat cat gaa aac gcc aac aaa att ctg aat cgg cca         48
Thr Val Phe Leu Asp His Glu Asn Ala Asn Lys Ile Leu Asn Arg Pro
 1               5                  10                  15 aag agg tat aat tca ggt aaa ttg gaa gag ttt gtt caa ggg aac ctt         96
Lys Arg Tyr Asn Ser Gly Lys Leu Glu Glu Phe Val Gln Gly Asn Leu
             20                  25                  30 gag aga gaa tgt atg gaa gaa aag tgt agt ttt gaa gaa gca cga gaa        144
Glu Arg Glu Cys Met Glu Glu Lys Cys Ser Phe Glu Glu Ala Arg Glu
         35                  40                  45 gtt ttt gaa aac act gaa aga aca act gaa ttt tgg aag cag tat gtt        192
Val Phe Glu Asn Thr Glu Arg Thr Thr Glu Phe Trp Lys Gln Tyr Val
     50                  55                  60 gat gga gat cag tgt gag tcc aat cca tgt tta aat ggc ggc agt tgc        240
Asp Gly Asp Gln Cys Glu Ser Asn Pro Cys Leu Asn Gly Gly Ser Cys
 65                  70                  75                  80 aag gat gac att aat tcc tat gaa tgt tgg tgt ccc ttt gga ttt gaa        288
Lys Asp Asp Ile Asn Ser Tyr Glu Cys Trp Cys Pro Phe Gly Phe Glu
                 85                  90                  95 gga aag aac tgt gaa tta gat gta aca tgt aac att aag aat ggc aga        336
Gly Lys Asn Cys Glu Leu Asp Val Thr Cys Asn Ile Lys Asn Gly Arg
            100                 105                 110 tgc gag cag ttt tgt aaa aat agt gct gat aac aag gtc gtt tgc tcc        384
Cys Glu Gln Phe Cys Lys Asn Ser Ala Asp Asn Lys Val Val Cys Ser
        115                 120                 125 tgt act gag gga tat cga ctt gca gaa aac cag aag tcc tgt gaa cca        432
Cys Thr Glu Gly Tyr Arg Leu Ala Glu Asn Gln Lys Ser Cys Glu Pro
    130                 135                 140 gca gtg cca ttt cca tgt gga aga gtt tct gtt tca caa act tct aag        480
Ala Val Pro Phe Pro Cys Gly Arg Val Ser Val Ser Gln Thr Ser Lys
145                 150                 155                 160 ctc acc cgt gct gag act gtt ttt cct gat gtg gac tat gta aat tct        528
Leu Thr Arg Ala Glu Thr Val Phe Pro Asp Val Asp Tyr Val Asn Ser
                165                 170                 175 act gaa gct gaa acc att ttg gat aac atc act caa agc acc caa tca        576
Thr Glu Ala Glu Thr Ile Leu Asp Asn Ile Thr Gln Ser Thr Gln Ser
            180                 185                 190 ttt aat gac ttc act cgg gtt gtt ggt gga gaa gat gcc aaa cca ggt        624
Phe Asn Asp Phe Thr Arg Val Val Gly Gly Glu Asp Ala Lys Pro Gly
        195                 200                 205 caa ttc cct tgg cag gtt gtt ttg aat ggt aaa gtt gat gca ttc tgt        672
Gln Phe Pro Trp Gln Val Val Leu Asn Gly Lys Val Asp Ala Phe Cys
    210                 215                 220 gga ggc tct atc gtt aat gaa aaa tgg att gta act gct gcc cac tgt        720
Gly Gly Ser Ile Val Asn Glu Lys Trp Ile Val Thr Ala Ala His Cys
225                 230                 235                 240 gtt gaa act ggt gtt aaa att aca gtt gtc gca ggt gaa cat aat att        768
Val Glu Thr Gly Val Lys Ile Thr Val Val Ala Gly Glu His Asn Ile
                245                 250                 255 gag gag aca gaa cat aca gag caa aag cga aat gtg att cga att att        816
Glu Glu Thr Glu His Thr Glu Gln Lys Arg Asn Val Ile Arg Ile Ile
            260                 265                 270 cct cac cac aac tac aat gca gct att aat aag tac aac cat gac att        864
Pro His His Asn Tyr Asn Ala Ala Ile Asn Lys Tyr Asn His Asp Ile
        275                 280                 285
```

```
gcc ctt ctg gaa ctg gac gaa ccc tta gtg cta aac agc tac gtt aca      912
Ala Leu Leu Glu Leu Asp Glu Pro Leu Val Leu Asn Ser Tyr Val Thr
    290                 295                 300 cct att tgc att gct gac aag gaa tac acg aac atc ttc ctc aaa ttt      960
Pro Ile Cys Ile Ala Asp Lys Glu Tyr Thr Asn Ile Phe Leu Lys Phe
305                 310                 315                 320 gga tct ggc tat gta agt ggc tgg gga aga gtc ttc cac aaa ggg aga     1008
Gly Ser Gly Tyr Val Ser Gly Trp Gly Arg Val Phe His Lys Gly Arg
                325                 330                 335 tca gct tta gtt ctt cag tac ctt aga gtt cca ctt gtt gac cga gcc     1056
Ser Ala Leu Val Leu Gln Tyr Leu Arg Val Pro Leu Val Asp Arg Ala
    340                 345                 350 aca tgt ctt cga tct aca aag ttc acc atc tat aac aac atg ttc tgt     1104
Thr Cys Leu Arg Ser Thr Lys Phe Thr Ile Tyr Asn Asn Met Phe Cys
355                 360                 365 gct ggc ttc cat gaa gga ggt aga gat tca tgt caa gga gat agt ggg     1152
Ala Gly Phe His Glu Gly Gly Arg Asp Ser Cys Gln Gly Asp Ser Gly
                370                 375                 380 gga ccc cat gtt act gaa gtg gaa ggg acc agt ttc tta act gga att     1200
Gly Pro His Val Thr Glu Val Glu Gly Thr Ser Phe Leu Thr Gly Ile
385                 390                 395                 400 att agc tgg ggt gaa gag tgt gca atg aaa ggc aaa tat gga ata tat     1248
Ile Ser Trp Gly Glu Glu Cys Ala Met Lys Gly Lys Tyr Gly Ile Tyr
            405                 410                 415 acc aag gta tcc cgg tat gtc aac tgg att aag gaa aaa aca aag ctc     1296
Thr Lys Val Ser Arg Tyr Val Asn Trp Ile Lys Glu Lys Thr Lys Leu
        420                 425                 430 act taa tga aag atg gat ttc caa ggt taa ttc att gga att gaa aat     1344
Thr         Lys Met Asp Phe Gln Gly     Phe Ile Gly Ile Glu Asn
                    435                     440                 445 taa cag ggc ctc tca cta act aat cac ttt ccc atc ttt tgt tag att     1392
    Gln Gly Leu Ser Leu Thr Asn His Phe Pro Ile Phe Cys     Ile
                    450                 455 tga ata tat aca ttc tat gat cat tgc ttt ttc tct tta cag ggg aga     1440
    Ile Tyr Thr Phe Tyr Asp His Cys Phe Phe Ser Leu Gln Gly Arg
    460                 465                 470 att tca tat ttt acc tga gca aat tga tta gaa aat gga acc act aga     1488
Ile Ser Tyr Phe Thr     Ala Asn     Leu Glu Asn Gly Thr Thr Arg
475                 480                 485 gga ata taa tgt gtt agg aaa tta cag tca ttt cta agg gcc cag cct     1536
Gly Ile     Cys Val Arg Lys Leu Gln Ser Phe Leu Arg Ala Gln Pro
    490                 495                 500 tga caa att gtg agt aaa                                             1554
    Gln Ile Val Ser Lys
            505

<210> SEQ ID NO 14
<211> LENGTH: 433
<212> TYPE: PRT
<213> ORGANISM: Homo sapiens

<400> SEQUENCE: 14

Thr Val Phe Leu Asp His Glu Asn Ala Asn Lys Ile Leu Asn Arg Pro
1               5                   10                  15

Lys Arg Tyr Asn Ser Gly Lys Leu Glu Glu Phe Val Gln Gly Asn Leu
            20                  25                  30

Glu Arg Glu Cys Met Glu Glu Lys Cys Ser Phe Glu Glu Ala Arg Glu
        35                  40                  45

Val Phe Glu Asn Thr Glu Arg Thr Thr Glu Phe Trp Lys Gln Tyr Val
```

-continued

```
            50                  55                  60
Asp Gly Asp Gln Cys Glu Ser Asn Pro Cys Leu Asn Gly Gly Ser Cys
 65                  70                  75                  80
Lys Asp Asp Ile Asn Ser Tyr Glu Cys Trp Cys Pro Phe Gly Phe Glu
                 85                  90                  95
Gly Lys Asn Cys Glu Leu Asp Val Thr Cys Asn Ile Lys Asn Gly Arg
            100                 105                 110
Cys Glu Gln Phe Cys Lys Asn Ser Ala Asp Asn Lys Val Val Cys Ser
            115                 120                 125
Cys Thr Glu Gly Tyr Arg Leu Ala Glu Asn Gln Lys Ser Cys Glu Pro
        130                 135                 140
Ala Val Pro Phe Pro Cys Gly Arg Val Ser Val Ser Gln Thr Ser Lys
145                 150                 155                 160
Leu Thr Arg Ala Glu Thr Val Phe Pro Asp Val Asp Tyr Val Asn Ser
                165                 170                 175
Thr Glu Ala Glu Thr Ile Leu Asp Asn Ile Thr Gln Ser Thr Gln Ser
            180                 185                 190
Phe Asn Asp Phe Thr Arg Val Val Gly Gly Glu Asp Ala Lys Pro Gly
            195                 200                 205
Gln Phe Pro Trp Gln Val Val Leu Asn Gly Lys Val Asp Ala Phe Cys
        210                 215                 220
Gly Gly Ser Ile Val Asn Glu Lys Trp Ile Val Thr Ala Ala His Cys
225                 230                 235                 240
Val Glu Thr Gly Val Lys Ile Thr Val Val Ala Gly Glu His Asn Ile
                245                 250                 255
Glu Glu Thr Glu His Thr Glu Gln Lys Arg Asn Val Ile Arg Ile Ile
            260                 265                 270
Pro His His Asn Tyr Asn Ala Ala Ile Asn Lys Tyr Asn His Asp Ile
        275                 280                 285
Ala Leu Leu Glu Leu Asp Glu Pro Leu Val Leu Asn Ser Tyr Val Thr
290                 295                 300
Pro Ile Cys Ile Ala Asp Lys Glu Tyr Thr Asn Ile Phe Leu Lys Phe
305                 310                 315                 320
Gly Ser Gly Tyr Val Ser Gly Trp Gly Arg Val Phe His Lys Gly Arg
                325                 330                 335
Ser Ala Leu Val Leu Gln Tyr Leu Arg Val Pro Leu Val Asp Arg Ala
            340                 345                 350
Thr Cys Leu Arg Ser Thr Lys Phe Thr Ile Tyr Asn Asn Met Phe Cys
        355                 360                 365
Ala Gly Phe His Glu Gly Gly Arg Asp Ser Cys Gln Gly Asp Ser Gly
370                 375                 380
Gly Pro His Val Thr Glu Val Glu Gly Thr Ser Phe Leu Thr Gly Ile
385                 390                 395                 400
Ile Ser Trp Gly Glu Glu Cys Ala Met Lys Gly Lys Tyr Gly Ile Tyr
                405                 410                 415
Thr Lys Val Ser Arg Tyr Val Asn Trp Ile Lys Glu Lys Thr Lys Leu
            420                 425                 430
Thr
```

<210> SEQ ID NO 15
<211> LENGTH: 72
<212> TYPE: DNA
<213> ORGANISM: Homo sapiens
<220> FEATURE:

```
<221> NAME/KEY: CDS
<222> LOCATION: (1)..(72)

<400> SEQUENCE: 15 gct gag act gtt ttt cct gat gtg gac tat gta aat tct act gaa gct    48
Ala Glu Thr Val Phe Pro Asp Val Asp Tyr Val Asn Ser Thr Glu Ala
1               5                   10                  15 gaa acc att ttg gat aac atc act                                    72
Glu Thr Ile Leu Asp Asn Ile Thr
            20

<210> SEQ ID NO 16
<211> LENGTH: 24
<212> TYPE: PRT
<213> ORGANISM: Homo sapiens

<400> SEQUENCE: 16

Ala Glu Thr Val Phe Pro Asp Val Asp Tyr Val Asn Ser Thr Glu Ala
1               5                   10                  15

Glu Thr Ile Leu Asp Asn Ile Thr
            20

<210> SEQ ID NO 17
<211> LENGTH: 75
<212> TYPE: DNA
<213> ORGANISM: Homo sapiens
<220> FEATURE:
<221> NAME/KEY: CDS
<222> LOCATION: (1)..(75)

<400> SEQUENCE: 17 cgt gct gag act gtt ttt cct gat gtg gac tat gta aat tct act gaa    48
Arg Ala Glu Thr Val Phe Pro Asp Val Asp Tyr Val Asn Ser Thr Glu
1               5                   10                  15 gct gaa acc att ttg gat aac atc act                                75
Ala Glu Thr Ile Leu Asp Asn Ile Thr
            20                  25

<210> SEQ ID NO 18
<211> LENGTH: 25
<212> TYPE: PRT
<213> ORGANISM: Homo sapiens

<400> SEQUENCE: 18

Arg Ala Glu Thr Val Phe Pro Asp Val Asp Tyr Val Asn Ser Thr Glu
1               5                   10                  15

Ala Glu Thr Ile Leu Asp Asn Ile Thr
            20                  25

<210> SEQ ID NO 19
<211> LENGTH: 105
<212> TYPE: DNA
<213> ORGANISM: Homo sapiens
<220> FEATURE:
<221> NAME/KEY: CDS
<222> LOCATION: (1)..(105)

<400> SEQUENCE: 19 gct gag act gtt ttt cct gat gtg gac tat gta aat tct act gaa gct    48
Ala Glu Thr Val Phe Pro Asp Val Asp Tyr Val Asn Ser Thr Glu Ala
1               5                   10                  15 gaa acc att ttg gat aac atc act caa agc acc caa tca ttt aat gac    96
Glu Thr Ile Leu Asp Asn Ile Thr Gln Ser Thr Gln Ser Phe Asn Asp
            20                  25                  30
```

```
ttc act cgg                                                              105
Phe Thr Arg
        35

<210> SEQ ID NO 20
<211> LENGTH: 35
<212> TYPE: PRT
<213> ORGANISM: Homo sapiens

<400> SEQUENCE: 20

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg
        35

<210> SEQ ID NO 21
<211> LENGTH: 108
<212> TYPE: DNA
<213> ORGANISM: Homo sapiens
<220> FEATURE:
<221> NAME/KEY: CDS
<222> LOCATION: (1)..(108)

<400> SEQUENCE: 21 cgt gct gag act gtt ttt cct gat gtg gac tat gta aat tct act gaa        48
Arg Ala Glu Thr Val Phe Pro Asp Val Asp Tyr Val Asn Ser Thr Glu
1               5                   10                  15 gct gaa acc att ttg gat aac atc act caa agc acc caa tca ttt aat        96
Ala Glu Thr Ile Leu Asp Asn Ile Thr Gln Ser Thr Gln Ser Phe Asn
            20                  25                  30 gac ttc act cgg                                                         108
Asp Phe Thr Arg
        35

<210> SEQ ID NO 22
<211> LENGTH: 36
<212> TYPE: PRT
<213> ORGANISM: Homo sapiens

<400> SEQUENCE: 22

Arg Ala Glu Thr Val Phe Pro Asp Val Asp Tyr Val Asn Ser Thr Glu
1               5                   10                  15

Ala Glu Thr Ile Leu Asp Asn Ile Thr Gln Ser Thr Gln Ser Phe Asn
            20                  25                  30

Asp Phe Thr Arg
        35

<210> SEQ ID NO 23
<211> LENGTH: 1639
<212> TYPE: DNA
<213> ORGANISM: Homo sapiens
<220> FEATURE:
<221> NAME/KEY: CDS
<222> LOCATION: (2)..(1639)

<400> SEQUENCE: 23 t atg cag cgc gtg aac atg atc atg gca gaa tca cca ggc ctc atc acc      49
  Met Gln Arg Val Asn Met Ile Met Ala Glu Ser Pro Gly Leu Ile Thr
  1               5                   10                  15 atc tgc ctt tta gga tat cta ctc agt gct gaa tgt aca gtt ttt ctt        97
Ile Cys Leu Leu Gly Tyr Leu Leu Ser Ala Glu Cys Thr Val Phe Leu
            20                  25                  30
```

| | | |
|---|---|---|
| gat cat gaa aac gcc aac aaa att ctg aat cgg cca aag agg tat aat<br>Asp His Glu Asn Ala Asn Lys Ile Leu Asn Arg Pro Lys Arg Tyr Asn<br>      35                    40                    45 | 145 | |
| tca ggt aaa ttg gaa gag ttt gtt caa ggg aac ctt gag aga gaa tgt<br>Ser Gly Lys Leu Glu Glu Phe Val Gln Gly Asn Leu Glu Arg Glu Cys<br>      50                    55                    60 | 193 | |
| atg gaa gaa aag tgt agt ttt gaa gaa gca cga gaa gtt ttt gaa aac<br>Met Glu Glu Lys Cys Ser Phe Glu Glu Ala Arg Glu Val Phe Glu Asn<br>65                    70                    75                  80 | 241 | |
| act gaa aga aca act gaa ttt tgg aag cag tat gtt gat gga gat cag<br>Thr Glu Arg Thr Thr Glu Phe Trp Lys Gln Tyr Val Asp Gly Asp Gln<br>                    85                    90                  95 | 289 | |
| tgt gag tcc aat cca tgt tta aat ggc ggc agt tgc aag gat gac att<br>Cys Glu Ser Asn Pro Cys Leu Asn Gly Gly Ser Cys Lys Asp Asp Ile<br>                  100                 105                110 | 337 | |
| aat tcc tat gaa tgt tgg tgt ccc ttt gga ttt gaa gga aag aac tgt<br>Asn Ser Tyr Glu Cys Trp Cys Pro Phe Gly Phe Glu Gly Lys Asn Cys<br>                  115                 120                125 | 385 | |
| gaa tta gat gta aca tgt aac att aag aat ggc aga tgc gag cag ttt<br>Glu Leu Asp Val Thr Cys Asn Ile Lys Asn Gly Arg Cys Glu Gln Phe<br>      130                   135                 140 | 433 | |
| tgt aaa aat agt gct gat aac aag gtc gtt tgc tcc tgt act gag gga<br>Cys Lys Asn Ser Ala Asp Asn Lys Val Val Cys Ser Cys Thr Glu Gly<br>145                    150                 155                160 | 481 | |
| tat cga ctt gca gaa aac cag aag tcc tgt gaa cca gca gtg cca ttt<br>Tyr Arg Leu Ala Glu Asn Gln Lys Ser Cys Glu Pro Ala Val Pro Phe<br>                  165                 170                175 | 529 | |
| cca tgt gga aga gtt tct gtt tca caa act tct aag ctc acc cgt gct<br>Pro Cys Gly Arg Val Ser Val Ser Gln Thr Ser Lys Leu Thr Arg Ala<br>                  180                 185                190 | 577 | |
| gag act gtt ttt cct gat gtg gac tat gta aat tct act gaa gct gaa<br>Glu Thr Val Phe Pro Asp Val Asp Tyr Val Asn Ser Thr Glu Ala Glu<br>                195                 200                205 | 625 | |
| acc att ttg gat aac atc act caa agc acc caa tca ttt aat gac ttc<br>Thr Ile Leu Asp Asn Ile Thr Gln Ser Thr Gln Ser Phe Asn Asp Phe<br>      210                 215                 220 | 673 | |
| act cgg gtt gtt ggt gga gaa gat gcc aaa cca ggt caa ttc cct tgg<br>Thr Arg Val Val Gly Gly Glu Asp Ala Lys Pro Gly Gln Phe Pro Trp<br>225                    230                 235                240 | 721 | |
| cag gtt gtt ttg aat ggt aaa gtt gat gca ttc tgt gga ggc tct atc<br>Gln Val Val Leu Asn Gly Lys Val Asp Ala Phe Cys Gly Gly Ser Ile<br>                  245                 250                255 | 769 | |
| gtt aat gaa aaa tgg att gta act gct gcc cac tgt gtt gaa act ggt<br>Val Asn Glu Lys Trp Ile Val Thr Ala Ala His Cys Val Glu Thr Gly<br>                260                 265                270 | 817 | |
| gtt aaa att aca gtt gtc gca ggt gaa cat aat att gag gag aca gaa<br>Val Lys Ile Thr Val Val Ala Gly Glu His Asn Ile Glu Glu Thr Glu<br>            275                 280                285 | 865 | |
| cat aca gag caa aag cga aat gtg att cga att att cct cac cac aac<br>His Thr Glu Gln Lys Arg Asn Val Ile Arg Ile Ile Pro His His Asn<br>      290                 295                 300 | 913 | |
| tac aat gca gct att aat aag tac aac cat gac att gcc ctt ctg gaa<br>Tyr Asn Ala Ala Ile Asn Lys Tyr Asn His Asp Ile Ala Leu Leu Glu<br>305                    310                 315                320 | 961 | |
| ctg gac gaa ccc tta gtg cta aac agc tac gtt aca cct att tgc att<br>Leu Asp Glu Pro Leu Val Leu Asn Ser Tyr Val Thr Pro Ile Cys Ile<br>                  325                 330                335 | 1009 | |
| gct gac aag gaa tac acg aac atc ttc ctc aaa ttt gga tct ggc tat<br>Ala Asp Lys Glu Tyr Thr Asn Ile Phe Leu Lys Phe Gly Ser Gly Tyr | 1057 | |

```
gta agt ggc tgg gga aga gtc ttc cac aaa ggg aga tca gct tta gtt    1105
Val Ser Gly Trp Gly Arg Val Phe His Lys Gly Arg Ser Ala Leu Val
        355                 360                 365 ctt cag tac ctt aga gtt cca ctt gtt gac cga gcc aca tgt ctt cga    1153
Leu Gln Tyr Leu Arg Val Pro Leu Val Asp Arg Ala Thr Cys Leu Arg
370                 375                 380 tct aca aag ttc acc atc tat aac aac atg ttc tgt gct ggc ttc cat    1201
Ser Thr Lys Phe Thr Ile Tyr Asn Asn Met Phe Cys Ala Gly Phe His
385                 390                 395                 400 gaa gga ggt aga gat tca tgt caa gga gat agt ggg gga ccc cat gtt    1249
Glu Gly Gly Arg Asp Ser Cys Gln Gly Asp Ser Gly Gly Pro His Val
                405                 410                 415 act gaa gtg gaa ggg acc agt ttc tta act gga att att agc tgg ggt    1297
Thr Glu Val Glu Gly Thr Ser Phe Leu Thr Gly Ile Ile Ser Trp Gly
            420                 425                 430 gaa gag tgt gca atg aaa ggc aaa tat gga ata tat acc aag gta tcc    1345
Glu Glu Cys Ala Met Lys Gly Lys Tyr Gly Ile Tyr Thr Lys Val Ser
                435                 440                 445 cgg tat gtc aac tgg att aag gaa aaa aca aag ctc act taa tga aag    1393
Arg Tyr Val Asn Trp Ile Lys Glu Lys Thr Lys Leu Thr             Lys
450                 455                 460 atg gat ttc caa ggt taa ttc att gga att gaa aat taa cag ggc ctc    1441
Met Asp Phe Gln Gly     Phe Ile Gly Ile Glu Asn     Gln Gly Leu
        465                 470                 475 tca cta act aat cac ttt ccc atc ttt tgt tag att tga ata tat aca    1489
Ser Leu Thr Asn His Phe Pro Ile Phe Cys     Ile     Ile Tyr Thr
                480                 485                     490 ttc tat gat cat tgc ttt ttc tct tta cag ggg aga att tca tat ttt    1537
Phe Tyr Asp His Cys Phe Phe Ser Leu Gln Gly Arg Ile Ser Tyr Phe
                495                 500                 505 acc tga gca aat tga tta gaa aat gga acc act aga gga ata taa tgt    1585
Thr     Ala Asn     Leu Glu Asn Gly Thr Thr Arg Gly Ile     Cys
                        510                 515 gtt agg aaa tta cag tca ttt cta agg gcc cag cct tga caa att gtg    1633
Val Arg Lys Leu Gln Ser Phe Leu Arg Ala Gln Pro     Gln Ile Val
520                 525                 530 agt aaa                                                            1639
Ser Lys
535

<210> SEQ ID NO 24
<211> LENGTH: 461
<212> TYPE: PRT
<213> ORGANISM: Homo sapiens

<400> SEQUENCE: 24

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95
```

```
Cys Glu Ser Asn Pro Cys Leu Asn Gly Gly Ser Cys Lys Asp Asp Ile
             100                 105                 110

Asn Ser Tyr Glu Cys Trp Cys Pro Phe Gly Phe Glu Gly Lys Asn Cys
         115                 120                 125

Glu Leu Asp Val Thr Cys Asn Ile Lys Asn Gly Arg Cys Glu Gln Phe
     130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                 165                 170                 175

Pro Cys Gly Arg Val Ser Val Ser Gln Thr Ser Lys Leu Thr Arg Ala
             180                 185                 190

Glu Thr Val Phe Pro Asp Val Asp Tyr Val Asn Ser Thr Glu Ala Glu
         195                 200                 205

Thr Ile Leu Asp Asn Ile Thr Gln Ser Thr Gln Ser Phe Asn Asp Phe
     210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                 245                 250                 255

Val Asn Glu Lys Trp Ile Val Thr Ala Ala His Cys Val Glu Thr Gly
             260                 265                 270

Val Lys Ile Thr Val Val Ala Gly Glu His Asn Ile Glu Glu Thr Glu
         275                 280                 285

His Thr Glu Gln Lys Arg Asn Val Ile Arg Ile Ile Pro His His Asn
     290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                 325                 330                 335

Ala Asp Lys Glu Tyr Thr Asn Ile Phe Leu Lys Phe Gly Ser Gly Tyr
             340                 345                 350

Val Ser Gly Trp Gly Arg Val Phe His Lys Gly Arg Ser Ala Leu Val
         355                 360                 365

Leu Gln Tyr Leu Arg Val Pro Leu Val Asp Arg Ala Thr Cys Leu Arg
     370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                 405                 410                 415

Thr Glu Val Glu Gly Thr Ser Phe Leu Thr Gly Ile Ile Ser Trp Gly
             420                 425                 430

Glu Glu Cys Ala Met Lys Gly Lys Tyr Gly Ile Tyr Thr Lys Val Ser
         435                 440                 445

Arg Tyr Val Asn Trp Ile Lys Glu Lys Thr Lys Leu Thr
     450                 455                 460

<210> SEQ ID NO 25
<211> LENGTH: 30
<212> TYPE: PRT
<213> ORGANISM: Artificial
<220> FEATURE:
<223> OTHER INFORMATION: Synthetic peptide

<400> SEQUENCE: 25
```

```
Ala Glu Thr Val Phe Ser Asn Met Asp Tyr Glu Asn Ser Thr Glu Ala
1               5                   10                  15

Val Phe Ile Gln Asp Asp Ile Thr Lys Lys Lys Lys Lys
                20                  25                  30

<210> SEQ ID NO 26
<211> LENGTH: 29
<212> TYPE: PRT
<213> ORGANISM: Artificial
<220> FEATURE:
<223> OTHER INFORMATION: Synthetic peptide

<400> SEQUENCE: 26

Thr Ile Asp Asp Gln Ile Phe Val Ala Glu Thr Ser Asn Glu Tyr Asp
1               5                   10                  15

Met Asn Ser Phe Val Thr Glu Ala Lys Lys Lys Lys Lys
                20                  25
```

THERAPEUTIC AGENT FOR EPITHELIAL AND ENDOTHELIAL INJURY

TECHNICAL FIELD

The present invention relates to a therapeutic agent for epithelial and endothelial injury, and in particular, a therapeutic agent for epithelial and endothelial microinjury, and a spread inducer of epithelial and endothelial cells, etc.

BACKGROUND ART

Blood coagulation factor IX (F9) associated with hemostasis and coagulation is an essential blood coagulation factor that has been classically known, and it is well known as a causal protein of hemophilia. During the process of a blood coagulation reaction, F9 is cleaved at an intermediate portion (Activation peptide (F9-AP)) existing between the light chain and the heavy chain by blood coagulation factor XI (F11) and blood coagulation factor VII, and it then becomes activated. Even after the cleavage, the light chain is linked to the heavy chain via a disulfide bond, and F9 promotes blood coagulation as a single molecule (Non Patent Literature 1: Textbook of Medical Physiology, 10e. Arthur C. Guyton MD). However, there are almost no reports regarding the functions of F9-AP, which is an intermediate portion.

It should be noted that vascular endothelial cells, which constitute one type of epithelial cell, generally control platelet functions or the coagulation and fibrinolytic system, and act to prevent thrombus formation in the blood vessel. In addition, the inner surfaces of the blood vessels are coated with vascular endothelial cells, and this prevents the leakage of blood or the components thereof from the blood vessels. Various acute diseases result from damage to vascular endothelial cells (Non Patent Literature 2: Harrison's Principles of Internal Medicine, 18e. Dan Longo). Examples of the diseases resulting from damage to vascular endothelial cells include: acute coronary syndrome (ACS) such as myocardial infarction; disseminated intravascular coagulation syndrome (DIC), in which blood coagulation reactions that should occur only at bleeding sites randomly occur in the blood vessels throughout the whole body; septicemia, which is a systemic inflammatory response syndrome caused by bacteria; and anaphylaxis, which is an allergic disease exhibiting the most severe symptoms among allergic diseases. In these diseases, the extent of injury of endothelial cells is small. However, abnormal coagulation in blood vessels and the leakage of blood components from blood vessels occur. Since these symptoms are acute and severe, prompt and appropriate measures and administration of a therapeutic agent are required. In order to treat the acute stage of the aforementioned diseases, administration of an antihypertensive agent, anti-histamine, steroid, an anticoagulant drug, and other agents, as well as invasive treatments such as bypass surgery have been conventionally carried out. Although the above-mentioned diseases have each different causes, injury of vascular endothelial cells and the leakage of plasma components to stroma caused thereby are turning points for the determination of the prognosis of the diseases. Accordingly, it has been desired in clinical sites to develop a therapeutic agent capable of promptly repairing epithelial and endothelial injury and improving the functions thereof. However, none of the conventional therapeutic agents for epithelial and endothelial injury have provided prompt therapeutic effects.

SUMMARY OF INVENTION

Under such circumstances, it has been desired to develop a therapeutic agent capable of promptly and effectively treating epithelial and endothelial injury, and in particular, epithelial and endothelial microinjury, and the like.

The present invention has been completed, taking into consideration the aforementioned circumstances. The present invention provides a therapeutic agent for epithelial and endothelial injury, a spread inducer of epithelial and endothelial cells, a pharmaceutical composition comprising the aforementioned therapeutic agent or spread inducer (e.g., a pharmaceutical composition for use in the treatment of diseases or pathological conditions associated with epithelial and endothelial injury), and the like, as described below.

(1) A peptide of any one of the following (a) to (f), a derivative thereof, or their salt:

(a) a peptide comprising the amino acid sequence shown in any one of SEQ ID NOS: 10, 4, 12 and 6;

(b) a peptide comprising the amino acid sequence shown in any one of SEQ ID NOS: 16, 18, 20 and 22;

(c) a peptide, which comprises an amino acid sequence having a deletion, substitution or addition of one or several amino acids with respect to the amino acid sequence shown in any one of 10, 4, 12 and 6, and which has an activity of repairing epithelial and endothelial injury or an activity of inducing spread of epithelial and endothelial cells;

(d) a peptide, which comprises an amino acid sequence having a deletion, substitution or addition of one or several amino acids with respect to the amino acid sequence shown in any one of 16, 18, 20 and 22, and which has an activity of repairing epithelial and endothelial injury or an activity of inducing spread of epithelial and endothelial cells;

(e) a peptide, which comprises an amino acid sequence having homology of 80% or more with the amino acid sequence shown in any one of 10, 4, 12 and 6, and which has an activity of repairing epithelial and endothelial injury or an activity of inducing spread of epithelial and endothelial cells; and (f) a peptide, which comprises an amino acid sequence having homology of 80% or more with the amino acid sequence shown in any one of 16, 18, 20 and 22, and which has an activity of repairing epithelial and endothelial injury or an activity of inducing spread of epithelial and endothelial cells.

In the peptide according to (1) above, a derivative thereof, or their salt, the epithelial and endothelial injury is, for example, microinjury.

(2) A therapeutic agent for epithelial and endothelial injury, which comprises a peptide of any one of the following (a) to (f), a derivative thereof, or their salt:

(a) a peptide comprising the amino acid sequence shown in any one of SEQ ID NOS: 10, 4, 12 and 6;

(b) a peptide comprising the amino acid sequence shown in any one of SEQ ID NOS: 16, 18, 20 and 22;

(c) a peptide, which comprises an amino acid sequence having a deletion, substitution or addition of one or several amino acids with respect to the amino acid sequence shown in any one of 10, 4, 12 and 6, and which has an activity of repairing epithelial and endothelial injury;

(d) a peptide, which comprises an amino acid sequence having a deletion, substitution or addition of one or several amino acids with respect to the amino acid sequence shown in any one of 16, 18, 20 and 22, and which has an activity of repairing epithelial and endothelial injury;

(e) a peptide, which comprises an amino acid sequence having homology of 80% or more with the amino acid sequence shown in any one of 10, 4, 12 and 6, and which has an activity of repairing epithelial and endothelial injury; and (f) a peptide, which comprises an amino acid sequence having homology of 80% or more with the amino acid sequence shown in any one of 16, 18, 20 and 22, and which has an activity of repairing epithelial and endothelial injury.

In the therapeutic agent according to (2) above, the epithelial and endothelial injury is, for example, microinjury.

(3) A spread inducer of epithelial and endothelial cells, which comprises a peptide of any one of the following (a) to (f), a derivative thereof, or their salt:

(a) a peptide comprising the amino acid sequence shown in any one of SEQ ID NOS: 10, 4, 12 and 6;

(b) a peptide comprising the amino acid sequence shown in any one of SEQ ID NOS: 16, 18, 20 and 22;

(c) a peptide, which comprises an amino acid sequence having a deletion, substitution or addition of one or several amino acids with respect to the amino acid sequence shown in any one of 10, 4, 12 and 6, and which has an activity of inducing spread of epithelial and endothelial cells;

(d) a peptide, which comprises an amino acid sequence having a deletion, substitution or addition of one or several amino acids with respect to the amino acid sequence shown in any one of 16, 18, 20 and 22, and which has an activity of inducing spread of epithelial and endothelial cells;

(e) a peptide, which comprises an amino acid sequence having homology of 80% or more with the amino acid sequence shown in any one of 10, 4, 12 and 6, and which has an activity of inducing spread of epithelial and endothelial cells; and (f) a peptide, which comprises an amino acid sequence having homology of 80% or more with the amino acid sequence shown in any one of 16, 18, 20 and 22, and which has an activity of inducing spread of epithelial and endothelial cells.

(4) A method for inducing spread of epithelial and endothelial cells, which comprises administering the spread inducer according to (3) above to a test animal.

(5) A pharmaceutical composition comprising the therapeutic agent according to (2) above or the spread inducer according to (3) above.

An example of the pharmaceutical composition according to (5) above is a pharmaceutical composition for use in the treatment of diseases or pathological conditions associated with epithelial and endothelial injury. Herein, the epithelial and endothelial injury is, for example, microinjury. An example of the diseases or pathological conditions is at least one selected from the group consisting of septicemia, arteriosclerosis, acute myocardial infarction, angina, artery vein thrombosis, brain edema in cerebral vascular disease, bronchial asthma, and increased vascular permeability.

(6) A method for treating diseases or pathological conditions associated with epithelial and endothelial injury, which comprises administering the pharmaceutical composition according to (5) above to a test animal.

In the method according to (6) above, the epithelial and endothelial injury is, for example, microinjury. An example of the diseases or pathological conditions is at least one selected from the group consisting of septicemia, arteriosclerosis, acute myocardial infarction, angina, artery vein thrombosis, brain edema in cerebral vascular disease, bronchial asthma, and increased vascular permeability.

According to the present invention, there can be provided a therapeutic agent for epithelial and endothelial injury, and in particular, a therapeutic agent for epithelial and endothelial microinjury. Also, the present invention is able to provide a spread inducer of epithelial and endothelial cells.

The aforementioned therapeutic agent and spread inducer are extremely useful in that these agents can be used for the treatment of various types of diseases or pathological conditions, which are associated with epithelial and endothelial injury (particularly, microinjury).

Moreover, taking into consideration action effects, the aforementioned therapeutic agent and spread inducer can also be used as intercellular adhesion enhancers or intercellular space closers. This matter can be understood, for example, from the after-mentioned results of Examples 4 and 8 of the present application, etc.

BRIEF DESCRIPTION OF DRAWINGS

The patent or application file contains at least one color drawing. Copies of this patent or patent application publication with color drawing will be provided by the USPTO upon request and payment of the necessary fee.

DESCRIPTION OF EMBODIMENTS

Figure 1:
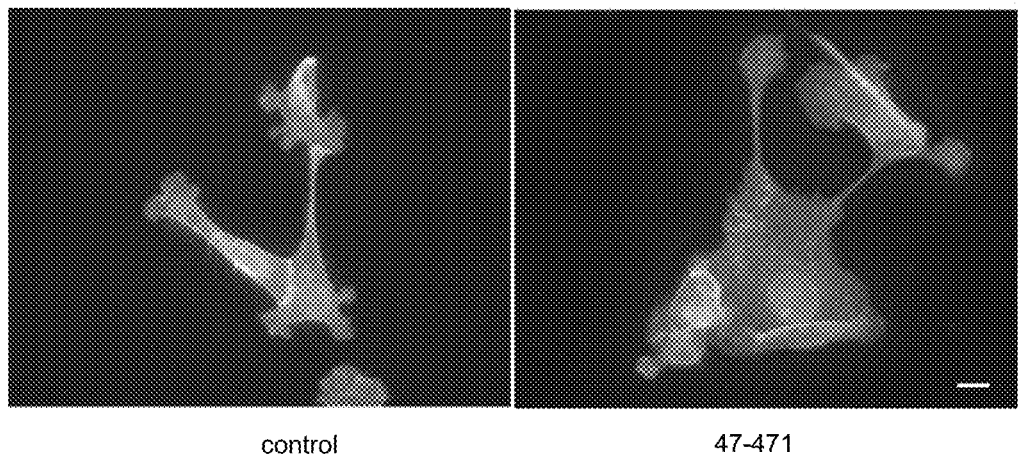
FIG. 1 includes photographs showing the results of Example 1 of the present application.

Hereinafter, the present invention will be described in detail. The scope of the present invention is not limited to the following explanation. The present invention, other than those described below, may be modified as appropriate and may be carried out in a range that does not impair the gist of the present invention.

The present description includes all of the contents as disclosed in the specification of Japanese Patent Application No. 2012-102910 (filed on Apr. 27, 2012), which is a priority document of the present application. In addition, all publications, for example, prior art publications, and patent literatures such as patent laid-open publications and patent publications, are incorporated herein by reference in their entirety.

1. Therapeutic Agent for Epithelial and Endothelial Injury, and Spread Inducer of Epithelial and Endothelial Cells The therapeutic agent for epithelial and endothelial injury of the present invention (hereinafter referred to as "the therapeutic agent of the present invention") and the spread inducer of epithelial and endothelial cells of the present invention (hereinafter referred to as "the spread inducer of the present invention") comprise a peptide at an intermediate portion (Activation peptide (F9-AP)) existing between the light chain and the heavy chain in the entire length of blood coagulation factor IX (F9), or a peptide including a partial fragment thereof, or the like.

The target of the treatment and spread induction by the therapeutic agent of the present invention and the spread inducer of the present invention may be epithelium or endothelium. Thus, the target is not particularly limited, and it is preferably endothelium. In particular, endothelial cells are more preferable, and vascular endothelial cells are even more preferable.

Moreover, in the present invention, the term "epithelial and endothelial injury" is used to mean injury to epithelial and endothelial tissues or epithelial and endothelial cells, and thus, it is not limited. However, the injury is preferably microinjury. In the present invention, the term "microinjury" can be defined as a space with a size from 1 μm or less (for example, 10 nm to 1 μm) to approximately 100 μm, which is created by a deletion of one or several cells, abnormality of intercellular adhesion, etc.

Furthermore, in the present invention, the term "extension of epithelial and endothelial cells" is defined as a phenomenon whereby the original cell shape of the aforementioned cell is extended and deformed to spread, and it then becomes to cover the range of a space or area that is larger than the ordinary state (the state of the cell before deformation).

The term "the entire length of F9" is used in the present invention to mean a peptide (protein) consisting of an amino acid sequence formed by removing, from the amino acid sequence of the whole F9 having a signal peptide and a propeptide, the signal peptide and propeptide portion.

For example, in the case of a mouse-derived peptide (protein), a peptide (protein) consisting of the amino acid sequence shown in SEQ ID NO: 2 (a total of 425 amino acids), which is formed by removing an amino acid sequence corresponding to the signal peptide and propeptide portion from the amino acid sequence of the whole F9 shown in SEQ ID NO: 8 (GenBank Accession No.: BAE28840; a total of 471 amino acids), corresponds to the entire length of F9. Since the region consisting of amino acids at positions 1 to 46 of the amino acid sequence shown in SEQ ID NO: 8 corresponds to the signal peptide and propeptide portion (the same applies in the present description), the amino acid sequence shown in SEQ ID NO: 2 consists of amino acids at positions 47 to 471 of the amino acid sequence shown in SEQ ID NO: 8. It is to be noted that the DNA encoding the peptide (protein) consisting of the amino acid sequence shown in SEQ ID NO: 8 is DNA consisting of nucleotides at positions 2 to 1414 (or at positions 2 to 1417) of the nucleotide sequence shown in SEQ ID NO: 7 (GenBank Accession No.: AK149372), and that the DNA encoding the peptide (protein) consisting of the amino acid sequence shown in SEQ ID NO: 2 is the nucleotide sequence shown in SEQ ID NO: 1 (namely, DNA consisting of nucleotides at positions 140 to 1414 (or at positions 140 to 1417) of the nucleotide sequence shown in SEQ ID NO: 7).

On the other hand, in the case of a human-derived peptide (protein), a peptide (protein) consisting of the amino acid sequence shown in SEQ ID NO: 14 (a total of 433 amino acids), which is formed by removing an amino acid sequence corresponding to the signal peptide and propeptide portion from the amino acid sequence of the whole F9 shown in SEQ ID NO: 24 (GenBank Accession No.: CAA01140.1; a total of 461 amino acids), corresponds to the entire length of F9. Since the region consisting of amino acids at positions 1 to 28 of the amino acid sequence shown in SEQ ID NO: 24 is the signal peptide and propeptide portion (the same applies in the present description), the amino acid sequence shown in SEQ ID NO: 14 consists of amino acids at positions 29 to 461 of the amino acid sequence shown in SEQ ID NO: 24. It is to be noted that the DNA encoding the peptide (protein) consisting of the amino acid sequence shown in SEQ ID NO: 24 is DNA consisting of nucleotides at positions 2 to 1384 (or at positions 2 to 1387) of the nucleotide sequence shown in SEQ ID NO: 23 (GenBank Accession No.: A13997.1), and that the DNA encoding the peptide (protein) consisting of the amino acid sequence shown in SEQ ID NO: 14 is the nucleotide sequence shown in SEQ ID NO: 13 (namely, DNA consisting of nucleotides at positions 86 to 1384 (or at positions 86 to 1387) of the nucleotide sequence shown in SEQ ID NO: 23).

As described above, the therapeutic agent of the present invention and the spread inducer of the present invention specifically comprise a peptide at an intermediate portion (F9-AP) existing between the light chain and the heavy chain in the entire length of F9 (for example, SEQ ID NOS: 2 and 14), or a partial fragment thereof. Specifically, these agents comprise the following peptide (a) or (b):

(a) a peptide comprising the amino acid sequence shown in any one of SEQ ID NOS: 10, 4, 12 and 6; or (b) a peptide comprising the amino acid sequence shown in any one of SEQ ID NOS: 16, 18, 20 and 22.

The aforementioned peptide (a) is not limited. It is preferably a peptide consisting of the amino acid sequence shown in any one of SEQ ID NOS: 10, 4, 12 and 6. Likewise, the aforementioned peptide (b) is not limited. It is preferably a peptide consisting of the amino acid sequence shown in any one of SEQ ID NOS: 16, 18, 20 and 22.

With regard to the aforementioned peptide (a), the amino acid sequences shown in SEQ ID NOS: 10, 4, 12 and 6 are all the amino acid sequences of partial fragments of mouse-derived F9. With regard to the aforementioned peptide (b), the amino acid sequences shown in SEQ ID NOS: 16, 18, 20 and 22 are all the amino acid sequences of partial fragments of human-derived F9.

Herein, the amino acid sequence shown in SEQ ID NO: 6 (45 amino acids) is the amino acid sequence of the peptide at the above-described intermediate portion (F9-AP) in mouse-derived F9. Likewise, the amino acid sequence shown in SEQ ID NO: 22 (36 amino acids) is the amino acid sequence of the peptide at the above-described intermediate portion (F9-AP) in human-derived F9.

The amino acid sequences shown in SEQ ID NOS: 4 and 18 are amino acid sequences consisting of 25 amino acids on the N-terminal side of the amino acid sequences shown in SEQ ID NOS: 6 and 22, respectively.

In addition, the amino acid sequences shown in SEQ ID NOS: 12 and 20 are amino acid sequences formed by removing one amino acid (Arg: arginine) on the N-terminal side of the amino acid sequences shown in SEQ ID NOS: 6 and 22, respectively.

Moreover, the amino acid sequences shown in SEQ ID NOS: 10 and 16 are amino acid sequences each consisting of 24 amino acids, which are formed by removing one amino acid (Arg: arginine) on the N-terminal side of the amino acid sequences shown in SEQ ID NOS: 4 and 18, respectively.

Peptides each consisting of the above-described 25 amino acid residues shown in SEQ ID NOS: 4 and 18, and in particular, peptides each consisting of 24 amino acids residues shown in SEQ ID NOS: 10 and 16, are portions corresponding to the active sites of the above-described intermediate portions (F9-AP) in mouse- and human-derived F9. Herein, the mouse-derived amino acid sequence shown in SEQ ID NO: 10, which corresponds to the aforementioned active site, has high homology with the human-derived amino acid sequence shown in SEQ ID NO: 16, which corresponds to the aforementioned active site. Also, the amino acid sequences of, at least, mammals show high homology with one another. Therefore, when a peptide comprising, for example, a mouse-derived amino acid sequence has been confirmed to have an activity of repairing epithelial and endothelial injury or an activity of inducing spread of epithelial and endothelial cells, a person skilled in the art could have rationally and naturally assumed that a peptide comprising an amino acid sequence derived from another mammal, and in particular, from a human could also have the above-described epithelial and endothelial injury repairing activity or spread-inducing activity.

Furthermore, the amino acid sequence shown in SEQ ID NO: 4 is a sequence consisting of 25 amino acids at positions 192 to 216 of the amino acid sequence shown in SEQ ID NO: 8 that is the whole F9 derived from mice; the amino acid sequence shown in SEQ ID NO: 10 is a sequence consisting of 24 amino acids at positions 193 to 216 of the amino acid sequence shown in SEQ ID NO: 8; the amino acid sequence shown in SEQ ID NO: 6 is a sequence consisting of 45 amino acids at positions 192 to 236 of the amino acid sequence shown in SEQ ID NO: 8; and the amino acid sequence shown in SEQ ID NO: 12 is a sequence consisting of 44 amino acids at positions 193 to 236 of the amino acid sequence shown in SEQ ID NO: 8. It is to be noted that DNAs encoding the above-described peptides (proteins) consisting of the amino acid sequences shown in SEQ ID NOS: 10, 4, 12 and 6 are the nucleotide sequences shown in SEQ ID NOS: 9, 3, 11 and 5, respectively.

Similarly, the amino acid sequence shown in SEQ ID NO: 18 is a sequence consisting of 25 amino acids at positions 191 to 215 of the amino acid sequence shown in SEQ ID NO: 24 that is the whole F9 derived from humans; the amino acid sequence shown in SEQ ID NO: 16 is a sequence consisting of 24 amino acids at positions 192 to 215 of the amino acid sequence shown in SEQ ID NO: 24; the amino acid sequence shown in SEQ ID NO: 22 is a sequence consisting of 36 amino acids at positions 191 to 226 of the amino acid sequence shown in SEQ ID NO: 24; and the amino acid sequence shown in SEQ ID NO: 20 is a sequence consisting of 35 amino acids at positions 192 to 226 of the amino acid sequence shown in SEQ ID NO: 24. It is to be noted that DNAs encoding the above-described peptides (proteins) consisting of the amino acid sequences shown in SEQ ID NOS: 16, 18, 20 and 22 are the nucleotide sequences shown in SEQ ID NOS: 15, 17, 19 and 21, respectively.

In the present invention, the term "peptide" is used to mean a product constructed by binding at least two amino acids via a peptide bond. The present peptide includes an oligopeptide, a polypeptide, and the like. Further, a polypeptide that forms a certain three-dimensional structure is referred to as a "protein." In the present invention, such a protein is also included in the above-described "peptide." Accordingly, a peptide comprised in the therapeutic agent of the present invention and the spread inducer of the present invention may mean any one of an oligopeptide, a polypeptide and a protein.

Further, as described above, the therapeutic agent of the present invention and the spread inducer of the present invention may comprise, as peptides functionally equivalent to the above-described peptides (a) and (b), the following peptides (c) and (d):

(c) a peptide, which comprises an amino acid sequence having a deletion, substitution or addition of one or several amino acids with respect to the amino acid sequence shown in any one of 10, 4, 12 and 6, and which has an activity of repairing epithelial and endothelial injury or an activity of inducing spread of epithelial and endothelial cells; and (d) a peptide, which comprises an amino acid sequence having a deletion, substitution or addition of one or several amino acids with respect to the amino acid sequence shown in any one of 16, 18, 20 and 22, and which has an activity of repairing epithelial and endothelial injury or an activity of inducing spread of epithelial and endothelial cells.

Herein, an example of the aforementioned "amino acid sequence having a deletion, substitution or addition of one or several amino acids" is an amino acid sequence having a deletion, substitution or addition of for example, 1 to 15 amino acids, 1 to 14 amino acids, 1 to 13 amino acids, 1 to 12 amino acids, 1 to 11 amino acids, 1 to 10 amino acids, 1 to 9 amino acids, 1 to 8 amino acids, 1 to 7 amino acids, 1 to 6 amino acids (1 to several amino acids), 1 to 5 amino acids, 1 to 4 amino acids, 1 to 3 amino acids, 1 or 2 amino acids, or 1 amino acid. Thus, the number of amino acids to be deleted, substituted or added is not limited. In general, as the number of amino acids decreases, it becomes preferable. Introduction of the mutation such as deletion, substitution or addition can be carried out using a mutagenesis kit that utilizes a site-directed mutagenesis, such as GeneTailor™ Site-Directed Mutagenesis System (Invitrogen), or TaKaRa Site-Directed Mutagenesis System (Prime STAR (registered trademark) Mutagenesis Basal kit, Mutan(registered trademark)-Super Express Km, etc.; manufactured by Takara Bio Inc.). Further, whether or not the concerned peptide is a peptide, into which the above-described mutation such as deletion, substitution or addition has been introduced, can be confirmed by various types of amino acid sequence determination methods, and structural analysis methods involving X-ray, NMR, etc.

Still further, examples of the peptides functionally equivalent to the above-described peptides (a) and (b) include the following peptides (e) and (f):

(e) a peptide, which comprises an amino acid sequence having homology of 80% or more with the amino acid sequence shown in any one of 10, 4, 12 and 6, and which has an activity of repairing epithelial and endothelial injury or an activity of inducing spread of epithelial and endothelial cells; and (f) a peptide, which comprises an amino acid sequence having homology of 80% or more with the amino acid sequence shown in any one of 16, 18, 20 and 22, and which has an activity of repairing epithelial and endothelial injury or an activity of inducing spread of epithelial and endothelial cells.

More specifically, examples of the above-described peptides (e) and (f) include peptides, which each comprise an amino acid sequence having homology of approximately 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more, with the amino acid sequence shown in any one of SEQ ID NOS: 10, 4, 12 and 6 with regard to the peptide (a), or with the amino acid sequence shown in any one of SEQ ID NOS: 16, 18, 20 and 22 with regard to the peptide (b), and which each have an activity of repairing epithelial and endothelial injury or an activity of inducing spread of epithelial and endothelial cells. In general, as the aforementioned numerical value indicating homology increases, it becomes preferable.

In the present invention, the term "activity of repairing epithelial and endothelial injury" is used to mean an activity of recovering the coatability (integrity) of epithelial and endothelial cells in the epithelium and endothelium. This activity can be evaluated and measured, for example, by Wound healing assay, Permeability assay, an immunostaining method, etc.

Moreover, in the present invention, the term "activity of inducing spread of epithelial and endothelial cells" is used to mean an activity of extending the shape of individual epithelial and endothelial cells (in particular, cells existing around epithelial and endothelial injury), and more specifically, an activity of extending the area of a substrate coated with a single of the aforementioned epithelial and endothelial cells in the epithelium and endothelium. This activity can be measured, for example, by Wound healing assay, Permeability assay, an immunostaining method, etc.

With regard to the above-described peptides (a) to (f), which are comprised in the therapeutic agent of the present invention and the spread inducer of the present invention, the number of the constituent amino acid residues is not particularly limited, and it can be determined, as appropriate, in a range in which the predetermined activity (the activity of repairing epithelial and endothelial injury, or the activity of inducing spread of epithelial and endothelial cells) can be maintained.

The above-described peptides (a) to (f) may be either naturally occurring peptides, or artificial peptides obtained by chemical synthesis, and thus, they are not limited. When the peptides (a) to (f) are naturally occurring peptides, they are preferable because there are no adverse effects such as cytotoxicity or side effects in many cases.

Examples of such naturally occurring peptides include natural oligopeptides, polypeptides and proteins, and their fragments. Such naturally occurring peptides may be directly obtained from natural products according to a known recovery method and a known purification method. Otherwise, according to a known genetic recombination technique, a gene encoding the naturally occurring peptide may be incorporated into various types of expression vectors or the like, and the expression vector may be then introduced into a cell, so that the gene is allowed to express therein, and thereafter, the peptide may be obtained by a known recovery method and a known purification method. Alternatively, the naturally occurring peptide may be generated in a cell-free protein synthetic system, in which commercially available kits are used, such as reagent kits PROTEIOS™ (Toyobo Co., Ltd.) and TNT™ System (Promega) and synthesizers PG-Mate™ (Toyobo Co., Ltd.) and RTS (Roche Diagnostics), and thereafter, the generated peptide may be obtained by a known recovery method and a known purification method. Hence, the methods are not limited.

On the other hand, chemically synthesized peptides can be obtained by a known peptide synthetic method. Examples of such a synthetic method include an azide method, an acid chloride method, an acid anhydride method, a mixed acid anhydride method, a DCC method, an active ester method, a carboimidazole method, and an oxidation-reduction method. In addition, either a solid-phase synthetic method or a liquid-phase synthesis method can be applied to the synthesis of such peptides. A commercially available peptide synthesizer may also be used. After completion of the synthetic reaction, the peptide can be purified by a combined use of known purification methods such as chromatography.

The therapeutic agent of the present invention and the spread inducer of the present invention may comprise a derivative of any one of the above-described peptides (a) to (f), as well as any one of the peptides (a) to (f), or instead of them. The term "derivative" is used herein to mean all products that can be prepared from the peptides (a) to (f). Thus, examples of the derivative include a peptide in which some constituent amino acids are substituted with non-naturally occurring amino acids, and a peptide in which some constituent amino acids (mainly, the side chains thereof) are chemically modified.

The therapeutic agent of the present invention and the spread inducer of the present invention may comprise a salt of any one of the above-described peptides (a) to (f) and/or the derivatives thereof, as well as any one of the peptides (a) to (f) and/or the derivatives thereof, or instead of them. The salt is preferably a physiologically acceptable acid-added salt or basic salt. Examples of the acid-added salt include: salts with inorganic acids such as hydrochloric acid, phosphoric acid, hydrobromic acid, or sulfuric acid; and salts with organic acids such as acetic acid, formic acid, propionic acid, fumaric acid, maleic acid, succinic acid, tartaric acid, citric acid, malic acid, oxalic acid, benzoic acid, methanesulfonic acid, or benzenesulfonic acid. Examples of the basic salt include: salts with inorganic bases such as sodium hydroxide, potassium hydroxide, ammonium hydroxide, or magnesium hydroxide; and salts with organic bases such as caffeine, piperidine, trimethylamine, or pyridine.

Salts can be prepared using appropriate acids such as hydrochloric acid, or appropriate bases such as sodium hydroxide. For example, salts can be prepared by treating the peptides with acids or bases in water or in a liquid containing an inactive water-miscible organic solvent such as methanol, ethanol or dioxane, using standard protocols.

The therapeutic agent of the present invention and the spread inducer of the present invention may consist of any one of the above-described peptides (a) to (f), the derivative thereof, or their salt, or may comprise other components, as well as the peptide, the derivative thereof, or their salt. Thus, it is not limited. Examples of other components include buffer solutions such as PBS and Tris-HCl, and additives such as sodium azide and glycerol. When the therapeutic agent of the present invention and the spread inducer of the present invention comprise other components, the ratio of other components contained can be determined, as appropriate, in a range in which the predetermined activity of the peptide, the derivative thereof or their salt (the activity of repairing epithelial and endothelial injury, or the activity of inducing spread of epithelial and endothelial cells) is not significantly impaired. Specifically, when the above-described peptide is used in the form of a solution containing the peptide, the concentration of the peptide is not particularly limited, and it is preferably 0.3 ng/ml or more, more preferably 0.3 to 5 ng/ml, even more preferably 0.3 to 2 ng/ml, further preferably 0.4 to 1.5 ng/ml, particularly preferably 0.6 to 1 ng/ml, and most preferably 0.8 to 1 ng/ml.

It is to be noted that the present invention also includes an invention directly relating to any one of the above-described peptides (a) to (f), the derivative thereof, or their salt.

The present invention can provide a method for treating diseases or pathological conditions associated with epithelial and endothelial injury, which uses the therapeutic agent of the present invention. Likewise, the present invention can also provide a method for inducing spread of epithelial and endothelial cells, which uses the spread inducer of the present invention. These methods comprise a step of administering the therapeutic agent of the present invention or the spread inducer of the present invention to a test animal (including a patient). The methods may also comprise any steps other than the aforementioned step, and are not limited. The test animal is not limited, either. Examples of the test animal include various types of mammals including humans and non-human animals. The test animal is preferably a human. The administration method, usage and dose of the therapeutic agent of the present invention and the spread inducer of the present invention, and diseases or pathological conditions associated with epithelial and endothelial injury, are not limited. The after-mentioned explanation regarding a method for administering a pharmaceutical composition can be applied herein, as appropriate.

Moreover, in the present invention, taking into consideration action effects, the aforementioned therapeutic agent and spread inducer can also be used as intercellular adhesion enhancers or intercellular space closers, as described above. Furthermore, the present invention can also provide a method involving intracellular adhesion of epithelial and endothelial cells, in which the intercellular adhesion enhancer of the present invention is used (intercellular adhesion-reinforcing method), or a method of closing the intercellular space between epithelial and endothelial cells, in which the intercellular space closer of the present invention is used. The same explanation as that regarding the above-described therapeutic method or spread-inducing method can be applied to the steps, procedures and details of these methods.

When the therapeutic agent of the present invention, the spread inducer of the present invention, or the like is administered to the living body of a test animal, any one of the above-described peptides (a) to (f), which is the active ingredient of the agent, may be directly administered thereto, or it may also be introduced in the living body in the form of DNA encoding the peptide (gene transfer). Thus, the administration method is not limited. The DNA can be introduced into the living body of a test animal according to various types of known gene transfer methods such as a liposome method (lipoplex method), a polyplex method, a peptide method, an electroporation method (electric punch method), and a viral vector method.

2. DNA, Recombinant Vector, and Transformant
(1) DNA

The present invention includes an invention relating to DNA comprising a nucleotide sequence encoding any one of the above-described peptides (a) to (f). This DNA may be DNA consisting of a nucleotide sequence encoding the peptide (for example, the above-described DNA consisting of the nucleotide sequence shown in any one of SEQ ID NOS: 9, 3, 11 and 5, or DNA consisting of the nucleotide sequence shown in any one of SEQ ID NOS: 15, 17, 19 and 21), or it may also be DNA comprising, as a part thereof, the aforementioned nucleotide sequence and also comprising known nucleotide sequences necessary for gene expression (a transcriptional promoter, an SD sequence, a Kozak sequence, a terminator, etc.). Thus, the DNA is not limited. The type of a codon is not limited in a nucleotide sequence encoding the peptide. The nucleotide sequence may comprise, for example, a codon that is generally included in mammals such as humans after transcription, or a codon generally included in microbes such as *Escherichia coli* or yeast, plants, and the like. Hence, the nucleotide sequence can be selected or designed, as appropriate.

Moreover, the present invention also includes DNA, which is capable of hybridizing under stringent conditions with DNA consisting of a nucleotide sequence complementary to the DNA comprising the nucleotide sequence encoding any one of the above-described peptides (a) to (f), and which encodes a protein having an activity of repairing epithelial and endothelial injury or an activity of inducing spread of epithelial and endothelial cells. Herein, the stringent conditions indicate, for example, conditions in which the salt (sodium) concentration is 150 to 900 mM and the temperature is 55° C. to 75° C., and preferably, the salt (sodium) concentration is 150 to 200 mM and the temperature is 60° C. to 70° C.

Other than the above-described DNA, examples of the DNA capable of the aforementioned hybridization include: DNA consisting of the nucleotide sequence shown in SEQ ID NO: 3 or 5, when calculated in homology searching software such as FAST or BLAST, using a default parameter; and DNA having homology of approximately 60% or more, approximately 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more, with DNA encoding a peptide consisting of the amino acid sequence shown in SEQ ID NO: 4 or 6.

(2) Recombinant Vector Comprising DNA

The present invention also includes a recombinant vector obtained by ligating (inserting) the above-described DNA of the present invention to (into) a suitable vector. The vector, into which the DNA of the present invention is inserted, is not particularly limited, as long as it is capable of replicating in a host. Examples of the vector include plasmid DNA, phage DNA, and virus.

Examples of the plasmid DNA include a plasmid derived from *Escherichia coli*, a plasmid derived from *Bacillus subtilis*, and a plasmid derived from yeast. An example of the phage DNA is λ phage. Examples of the virus include adenovirus and retrovirus.

To the recombinant vector of the present invention, a cis-element such as an enhancer, a splicing signal, a poly-A additional signal, a ribosome-binding sequence (SD sequence), a selective marker gene, a reporter gene, and the like can be ligated, as desired, as well as a promoter and the DNA of the present invention. Examples of the selective marker gene include a dihydrofolate reductase gene, an ampicillin resistance gene, and a neomycin resistance gene. Examples of the reporter gene include the genes of a green fluorescent protein (GFP) or mutants thereof (fluorescent proteins such as EGFP, BFP, or YFP), luciferase, alkaline phosphatase, and LacZ.

(3) Transformant

The present invention also includes a transformant obtained by introducing the above-described recombinant vector of the present invention into a host such that a gene of interest can be expressed therein. The host is not limited, as long as it allows the DNA of the present invention to express therein. Examples of the host include bacteria, yeasts and the like, which are well known in the present technical field.

When a bacterium is used as a host, the recombinant vector of the present invention is capable of autonomously replicating in the bacterium, and at the same time, a promoter, a ribosome-binding sequence, the DNA of the present invention and a transcription termination sequence can be added to the bacterium. An example of such a bacterium is *Escherichia coli*. As a promoter, a lac promoter is used, for example. As methods of introducing a vector into a bacterium, various types of known introduction methods, for example, a calcium ion method can be applied.

When yeast is used as a host, *Saccharomyces cerevisiae* is used, for example. The promoter used in this case is not particularly limited, as long as it can be expressed in yeast. An example of such a promoter is a gall promoter. Examples of the method of introducing a vector into yeast include an electroporation method and a spheroplast method.

3. Pharmaceutical Composition

The therapeutic agent of the present invention and the spread inducer of the present invention are useful as active ingredients comprised in a pharmaceutical composition. It is to be noted that any one of the above-described peptides (a) to (f) can also be referred to as the "active ingredient."

The pharmaceutical composition of the present invention is not limited. The present pharmaceutical composition is useful, for example, as a pharmaceutical composition for use in the treatment of diseases or pathological conditions associated with epithelial and endothelial injury (in particular, microinjury). Specifically, the present pharmaceutical composition is preferably used as a pharmaceutical composition for use in the treatment of septicemia, pulmonary edema, arteriosclerosis, acute myocardial infarction, angina, artery vein thrombosis, brain edema in cerebral vascular disease, bronchial asthma, etc. Also, it is preferably used as a pharmaceutical composition for treating (suppressing) a state in which vascular permeation is increased due to allergy or the like (i.e., increased vascular permeability).

The pharmaceutical composition of the present invention can be provided in the form of a pharmaceutical composition comprising, as an active ingredient, the therapeutic agent of the present invention or the spread inducer of the present invention, and further comprising a pharmaceutically acceptable carrier.

Examples of the "pharmaceutically acceptable carrier" include an excipient, a diluent, an expander, a disintegrator, a stabilizer, a preservative, a buffer agent, an emulsifier, an aromatic agent, a coloring agent, a sweetener, a thickener, a flavoring agent, a solubilizer, and other additives. Using one or more types of such carriers, the pharmaceutical composition can be processed in the form of an injection, a liquid agent, a capsule agent, a suspension, an emulsion, a syrup agent, etc. These pharmaceutical compositions can be administered orally or parenterally. Another form of the pharmaceutical compositions for parenteral administration may be an injection comprising one or more active substances, which is prescribed by an ordinary method. Such an injection can be produced by dissolving or suspending the pharmaceutical composition in a pharmaceutically acceptable carrier such as a normal saline or a commercially available distilled water used for injections. In addition, when the therapeutic agent of the present invention or the spread inducer of the present invention, which is an active ingredient, is administered into a living body, a colloidal dispersion system can be used. The colloidal dispersion system is expected to have the effect of enhancing the stability of the aforementioned peptide in vivo or the effect of efficiently transporting the compound to a specific organ, tissue or cell. The colloidal dispersion system is not limited, as long as it is a commonly used system. Examples of the colloidal dispersion system include dispersion systems each comprising, as a base, polyethylene glycol, a polymer composite, a polymer aggregate, a nanocapsule, a microsphere, a bead, and a lipid including an oil-in-water emulsifier, a micelle, a mixed micelle and a liposome. Preferred examples of the colloidal dispersion system include a liposome and an artificial membrane vesicle having the effect of efficiently transporting the compound to a specific organ, tissue or cell.

The dose of the pharmaceutical composition of the present invention may be different depending on the age, sex, body weight and symptoms of a test animal (various types of mammals including humans and non-human animals, and preferably, humans), therapeutic effects, administration method, treating time, the type of the therapeutic agent of the present invention or the spread inducer of the present invention contained in the pharmaceutical composition, etc. In general, the present pharmaceutical composition can be administered in a dose range of 100 μg to 5000 mg per adult per administration, but the applied dose is not limited thereto.

When the pharmaceutical composition is administered in the form of an injection, for example, it can be administered to a human patient at a dose of 1 μg to 100 mg per kg of body weight per administration, once or divided over several administrations, on average, per day. Examples of the administration form include intravenous injection, subcutaneous injection, intradermal injection, intramuscular injection, and intraperitoneal injection. Among these, intravenous injection is preferable. Moreover, such an injection can be prepared in the form of a non-aqueous diluent (e.g., polyethylene glycol, vegetable oils such as olive oil, alcohols such as ethanol, etc.), a suspension or an emulsion in some cases. Such an injection can be sterilized by filtration sterilization using a filter, addition of a disinfectant, etc. The injection can be produced in the form of an injection prepared at the time of use. That is to say, an aseptic solid composition can be prepared by a freeze-drying method or the like, and it can be then dissolved in aseptic distilled water used for injections or in another solvent before use.

The present invention provides use of the therapeutic agent of the present invention for producing a pharmaceutical agent (drug) for treating diseases or pathological conditions associated with epithelial and endothelial injury (in particular, microinjury). In addition, the present invention provides a method for treating diseases or pathological conditions associated with epithelial and endothelial injury (in particular, microinjury), wherein the method is characterized in that it uses the therapeutic agent of the present invention (i.e., administration of the present therapeutic agent to a test animal or a patient). Moreover, the present invention provides use of the therapeutic agent of the present invention for treating diseases or pathological conditions associated with epithelial and endothelial injury (in particular, microinjury). Herein, specific examples of the diseases or pathological conditions are the same as those described above.

Likewise, the present invention provides use of the spread inducer of the present invention for producing a pharmaceutical agent (drug) for treating diseases or pathological conditions associated with epithelial and endothelial injury (in particular, microinjury). In addition, the present invention provides a method for treating diseases or pathological conditions associated with epithelial and endothelial injury (in particular, microinjury), wherein the method is characterized in that it uses the spread inducer of the present invention (i.e., administration of the present spread inducer to a test animal or a patient). Moreover, the present invention provides use of the spread inducer of the present invention for treating diseases or pathological conditions associated with epithelial and endothelial injury (in particular, microinjury). Herein, specific examples of the diseases or pathological conditions are the same as those described above.

4. Kit

The present invention also provides a kit for treating epithelial and endothelial injury and a kit for inducing spread of epithelial and endothelial cells, which are characterized in that they comprise the therapeutic agent of the present invention and the spread inducer of the present invention, respectively, as structural components thereof. The kit of the present invention enables the treatment of epithelial and endothelial injury (in particular, microinjury) or induction of spread of epithelial and endothelial cells. Thus, the present kit can be used effectively, for example, when diseases or pathological conditions associated with epithelial and endothelial injury (specifically, septicemia, pulmonary edema, arteriosclerosis, acute myocardial infarction, post-cerebral-infarction cerebral edema, bronchial asthma, etc.) are treated. Accordingly, the kit of the present invention is not only effective in the clinical discipline, but also it is extremely useful for various types of experiments and/or studies in the field of medicine and pharmaceutical sciences.

The kit of the present invention may also comprise various types of buffers, sterile water, various types of reaction vessels (an Eppendorf tube, etc.), a washing agent, a surfactant, various types of plates, an aseptic, various types of cell culture vessels, and experimental operation manual (instructions) and the like, as well as the therapeutic agent of the present invention or the spread inducer of the present invention, and thus, the components contained in the kit are not limited.

The present invention will be more specifically described in the following examples. However, these examples are not intended to limit the scope of the present invention.

In the following Examples 1 to 9, as peptides to be used in the therapeutic agent and spread inducer of the present invention, a peptide consisting of the whole F9 shown in SEQ ID NO: 2 (F9(47-471)), a peptide consisting of a partial fragment of the whole F9 shown in SEQ ID NO: 6 (F9(192-236)), and further, a peptide consisting of a partial fragment of the F9(192-236) shown in SEQ ID NO: 4 (F9(192-216)) were used. F9(47-471) is a peptide comprising F9(192-236) and F9(192-216) as portions thereof. Such peptides used in the therapeutic agent and spread inducer of the present invention can be used, as appropriate, in a form in which one or several lysine residues are added to the C-terminus and/or N-terminus. In the following Examples, these peptides were used as fusion proteins with alkaline phosphatase (AP). Hereinafter, individual fusion proteins are referred to as AP-F9(47-471), AP-F9(192-236), and AP-F9(192-216).

Specifically, individual fusion proteins were produced as follows. Using a known genetic recombination technique, cDNAs encoding the predetermined peptides (F9(47-471), F9(192-236) and F9(192-216)) (specifically, DNAs each consisting of any one of the nucleotide sequences shown in SEQ ID NOS: 1, 3 and 5) were each inserted into an AP expression vector (APtag4) such that they become fusion genes with the AP gene, thereby constructing recombinant vectors comprising the fusion genes. The thus constructed vectors were each introduced into CHO cells, so that the individual genes were allowed to expressed therein, followed by purification and other operations, so as to produce individual fusion proteins. The cDNA was obtained by designing primers, as appropriate, based on the known gene sequence of F9 (SEQ ID NO: 7) and then amplifying a desired cDNA fragment according to PCR. The obtained cDNA was incorporated into APtag4, and was then used.

EXAMPLE 1

The squamous carcinoma cells A431 (hereinafter referred to as "A431 cells") were sparsely seeded on a culture dish. After that, alkaline phosphatase (AP; negative control) or AP-F9(47-471) (1 pmol/ml) was added to a culture medium, and a culture was then carried out at 37° C. for 30 minutes. Thereafter, the cells were fixed with 4% paraformaldehyde, and were then stained with anti-E cadherin antibody (green), phalloidin (red), and Hoechst33342 (blue). Then, the resulting cells were examined by microscopic visualization. The results are shown in FIG. 1. It was confirmed that the cells were extended by addition of the peptide of the entire-length F9 (F9(47-471)). It is to be noted that the scale bar shown in the photograph (lower right) of FIG. 1 indicates 10 μm. In addition, in FIG. 1, the term "control" indicates the results obtained in a case in which AP was added, and the term "47-471" indicates the results obtained in a case in which AP-F9(47-471) was added.

EXAMPLE 2

Figure 2:
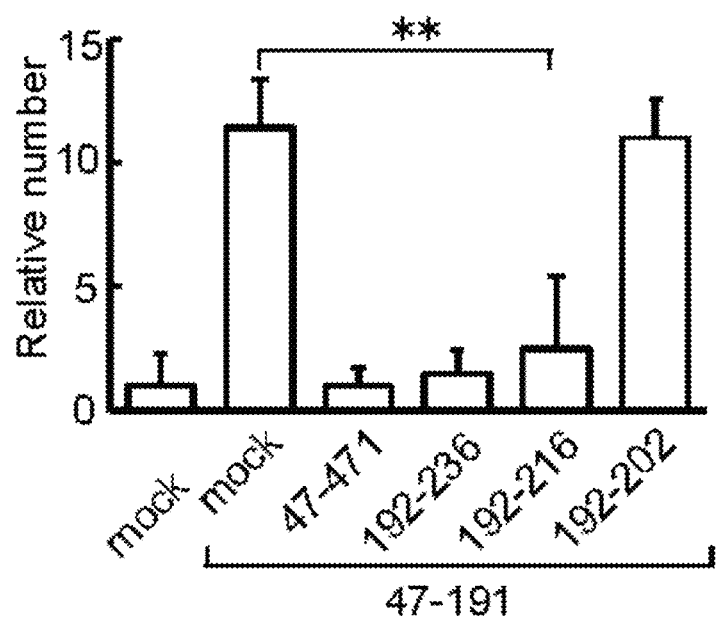
FIG. 2 is a graph showing the results of Example 2 of the present application. The numerical value of the vertical axis indicates the number of cells removed from the bottom surface when a culture dish was shaken.

A portion in the entire-length F9 (F9(47-471)), which has an activity of inducing spread of cells on a substrate, was determined using an ability to adhere to the substrate as an indicator. Specifically, A431 cells were seeded on a 96-well culture dish, and thereafter, an F9-derived peptide (F9(47-191)) (1 pmol/ml) having an action to inhibit adhesion between the cells and the substrate, and each of the peptides (F9(47-471), F9(192-236), F9(192-216) and F9(192-202)) (1 pmol/ml), were added to a culture medium. Thereafter, an F9 portion having an action to inhibit the aforementioned inhibitory action was examined under conditions in which a culture was performed at 37° C. for 24 hours and the culture dish was then shaken on a shaker. It is to be noted that F9(47-191) is a peptide consisting of amino acids at positions 47 to 191 in the amino acid sequence shown in SEQ ID NO: 8, and that F9(192-202) is a peptide consisting of amino acids at positions 192 to 202 in the amino acid sequence shown in SEQ ID NO: 8. The results are shown in FIG. 2. It was found that, among the aforementioned peptides examined in the present example, F9(192-216) was the shortest peptide (a peptide consisting of the smallest number of amino acid residues), which had an activity of inhibiting the inhibitory action on adhesion between the cells and the substrate, namely, an activity of inducing spread of the cells on the substrate. Each of the numerical values (on the vertical axis) in the graph of FIG. 2 is indicated as a mean±SD (**: $P<0.01$). In addition, in FIG. 2, the term "47-191" indicates the conditions in which F9(47-191) was added, and the terms "47-471," "192-236," "192-216," and "192-202" indicate the results obtained in the case of adding F9(47-471), F9(192-236), F9(192-216), and F9(192-202), respectively.

EXAMPLE 3

Figure 3:
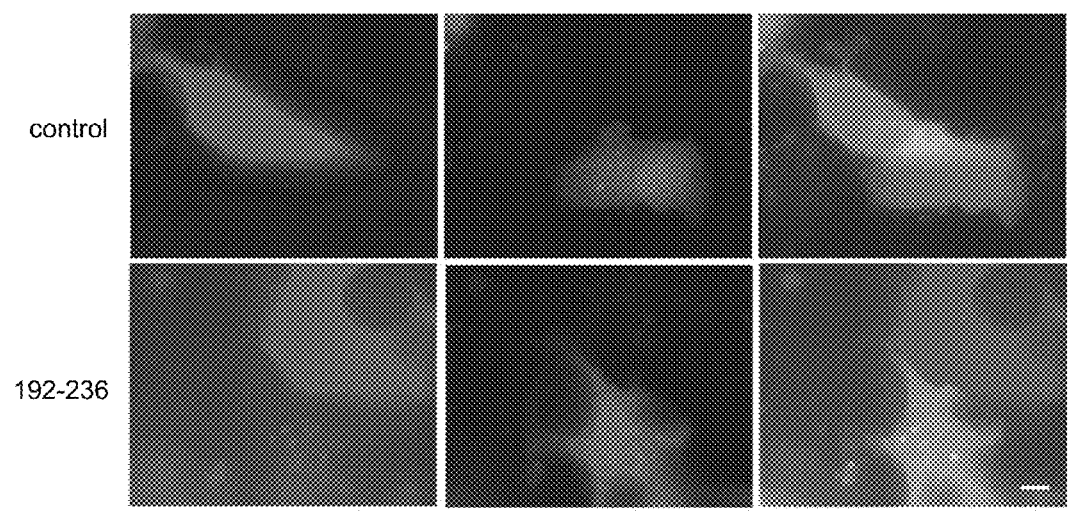
FIG. 3 includes photographs showing the results of Example 3 of the present application.

In order to examine the form of intercellular adhesion, a GFP (green) or RFP (red) gene was introduced into A431 cells according to a known genetic recombination technique, so as to produce transformed A431 cells which were transformed to express GFP or REP. Both types of the transformed cells were each seeded on a culture dish densely, and thereafter, AP (negative control) or AP-F9(192-236) (1 pmol/ml) was added to a culture medium, followed by performing a culture at 37° C. for 60 minutes. Thereafter, the cultured cells were fixed with 4% paraformaldehyde, and were then examined by microscopic visualization. The results are shown in FIG. 3. In the case of addition of the control, the shape of the resulting cells was that of mesenchymal cells, and the cells were partially overlapped with one another. On the other hand, in the case of addition of AP-F9(192-236), the resulting cells had an epithelioid angular shape, and the contact surface of the cells became linear, so that construction of an epithelioid structure was confirmed. The scale bar in the photograph (lower right) of FIG. 3 indicates 10 μM. In addition, in FIG. 3, the term "control" indicates the results obtained in the case of addition of AP, and the term "192-236" indicates the results obtained in the case of addition of AP-F9(192-236).

EXAMPLE 4

Figure 4:
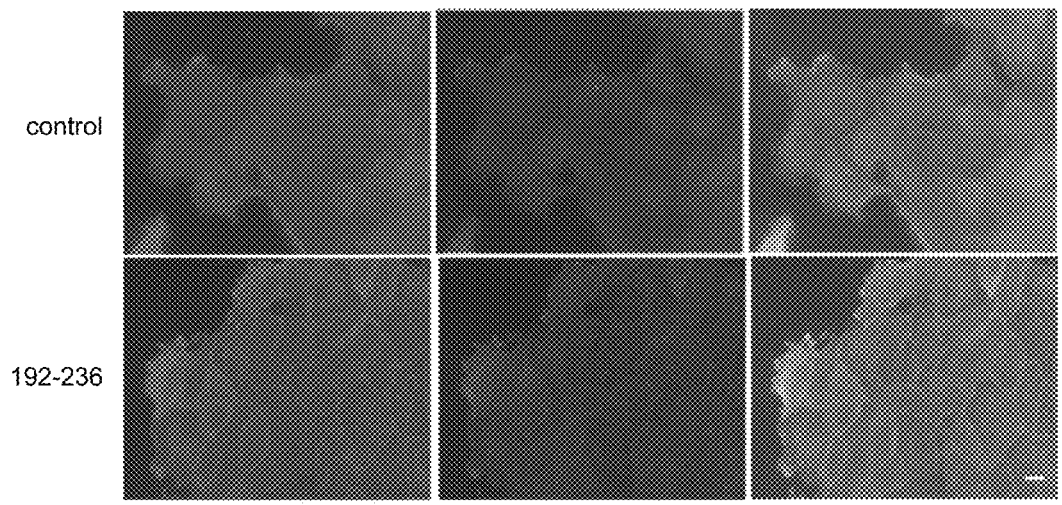
FIG. 4 includes photographs showing the results of Example 4 of the present application.

A431 cells were densely seeded on a culture dish, and a control (AP) or AP-F9(192-236) (1 pmol/ml) was then added to a culture medium, followed by performing a culture at 37° C. for 60 minutes. Thereafter, the cultured cells were fixed with 4% paraformaldehyde, and were then stained with an anti-E cadherin antibody (green) or an anti-β catenin antibody (red). After that, the resulting cells were examined by microscopic visualization. The results are shown in FIG. 4. It was confirmed that E cadherin or β catenin was localized in the intercellular adhesion portion, so that the adhesion was reinforced. The scale bar in the photograph (lower right) of FIG. 4 indicates 10 μm. In addition, in FIG. 4, the term "control" indicates the results obtained in the case of addition of AP, and the term "192-236" indicates the results obtained in the case of addition of AP-F9(192-236).

EXAMPLE 5

Figure 5:
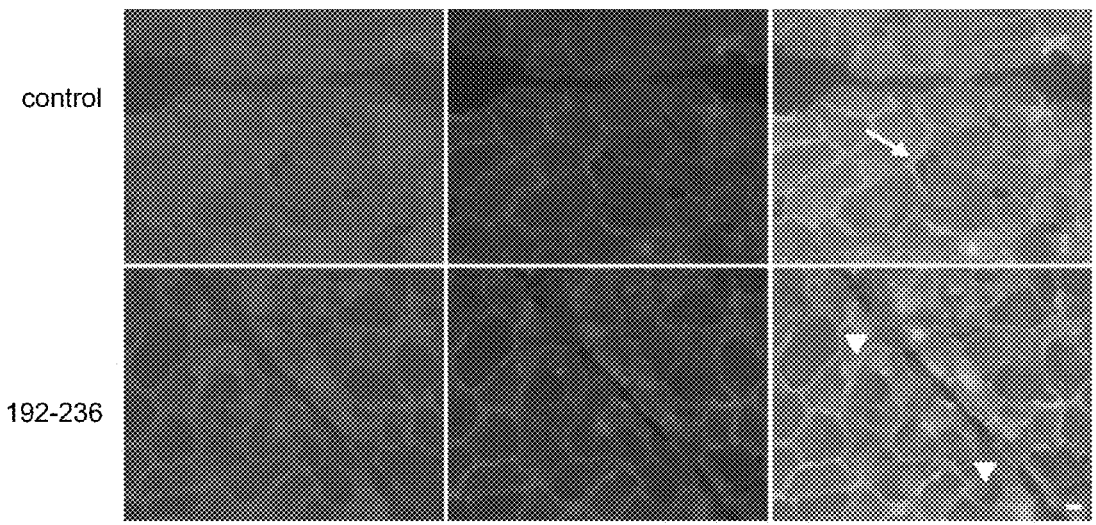
FIG. 5 includes photographs showing the results of Example 5 of the present application.

A431 cells were densely seeded on a culture dish, and AP (negative control) or AP-F9(192-236) (1 pmol/ml) was then added to a culture medium. Thereafter, the cells were damaged with a knife (wound size: approximately a width of one or two cells), and were then cultured at 37° C. for 30 minutes. Subsequently, the cultured cells were fixed with 4% paraformaldehyde, and were then stained with an anti-E cadherin antibody (green), phalloidin (red) or Hoechst33342 (blue), followed by performing microscopic visualization. The results are shown in FIG. 5. In the case of the control, cells located around the wound intended to migrate into the wound, and as a result, a hole (a space indicated with the arrow) was made between cells. In contrast, in the case of addition of AP-F9(192-236), it was confirmed that cells located around the wound were extended, and as a result, the wound was nearly closed up (∇). The scale bar in the photograph (lower right) of FIG. 5 indicates 10 μm. In addition, in FIG. 5, the term "control" indicates the results obtained in the case of addition of AP, and the term "192-236" indicates the results obtained in the case of addition of AP-F9(192-236).

EXAMPLE 6

Figure 6:
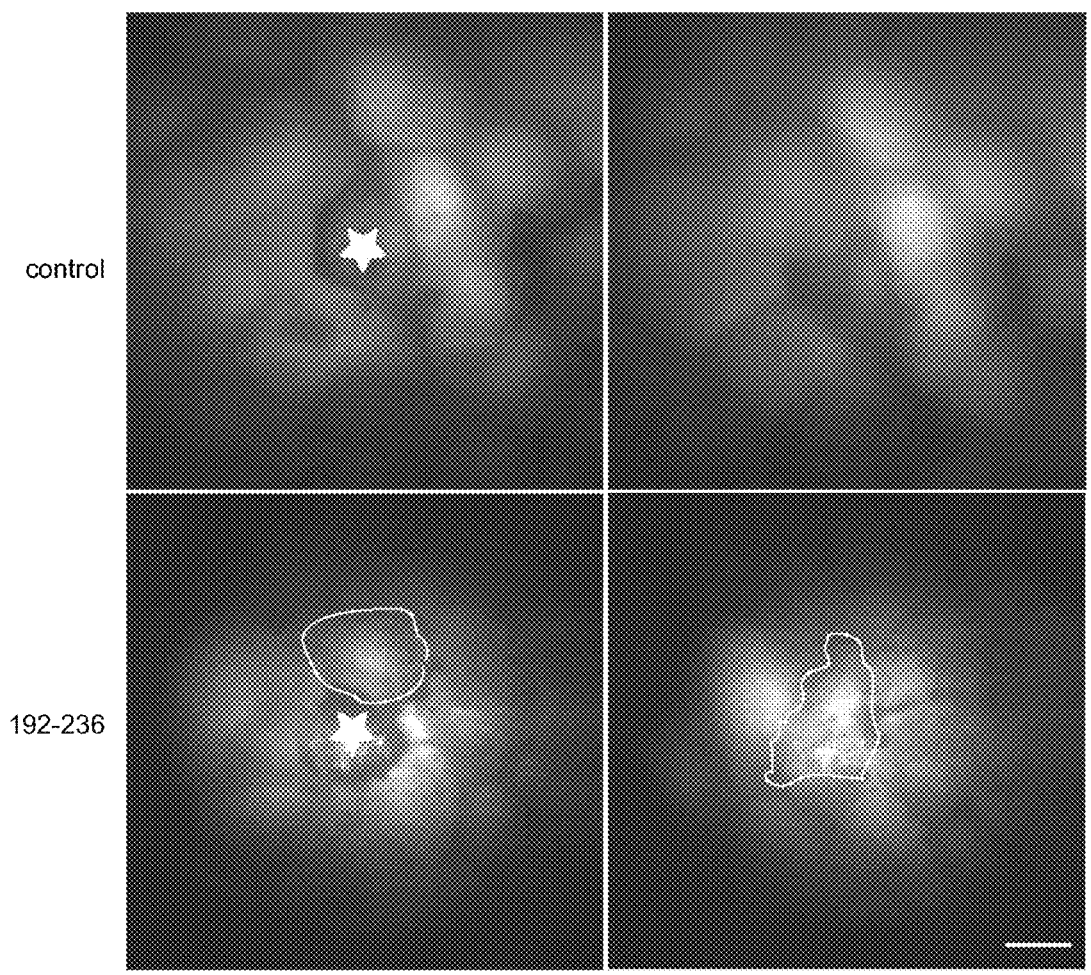
FIG. 6 includes photographs showing the results of Example 6 of the present application.

A431 cells were densely seeded on a culture dish, and the surviving cells were stained with fluorochrome. Thereafter, AP (negative control) or AP-F9(192-236) (1 pmol/ml) was added to a culture medium, and a single cell (asterisk) was then removed by needling it. Subsequently, while the cells were cultured at 37° C. for 60 minutes, they were observed over time by microscopic visualization. The results are shown in FIG. 6. In the case of addition of AP-F9(192-236), it was confirmed that cells located around the removed cell (which were marked with a white line) were extended 35 minutes after initiation of the culture, and that the hole was covered with the extended cells. The scale bar in the photograph (lower right) of FIG. 6 indicates 10 μm. In addition, in FIG. 6, the term "control" indicates the results obtained in the case of addition of AP, and the term "192-236" indicates the results obtained in the case of addition of AP-F9(192-236).

EXAMPLE 7

Figure 7:
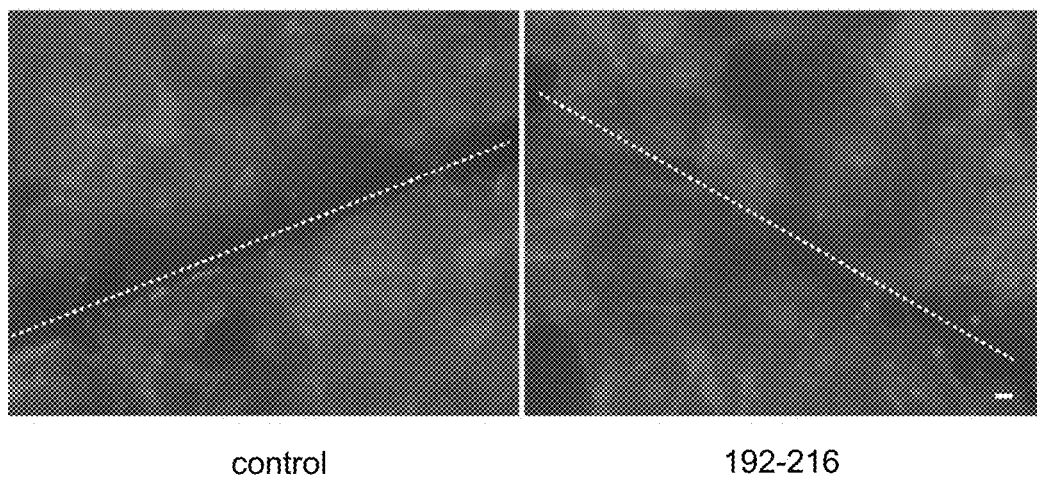
FIG. 7 includes photographs showing the results of Example 7 of the present application.

Bovine aortic endothelial cells (BAEC) were densely seeded on a culture dish. AP (negative control) or AP-F9 (192-216) (1 pmol/ml) was added to a culture medium. The cells were damaged with a knife (marked with a dotted line), and were then cultured at 37° C. for 30 minutes. Thereafter, the cultured cells were fixed with 4% paraformaldehyde, and were then stained with phalloidin (red) or Hoechst33342 (blue), followed by performing microscopic visualization. The results are shown in FIG. 7. In the case of addition of AP-F9(192-216), it was confirmed that cells located around the wound were extended and as a result, the wound was closed up. The scale bar in the photograph (lower right) of FIG. 7 indicates 10 μm. In addition, in FIG. 7, the term "control" indicates the results obtained in the case of addition of AP, and the term "192-216" indicates the results obtained in the case of addition of AP-F9(192-216).

EXAMPLE 8

Figure 8:
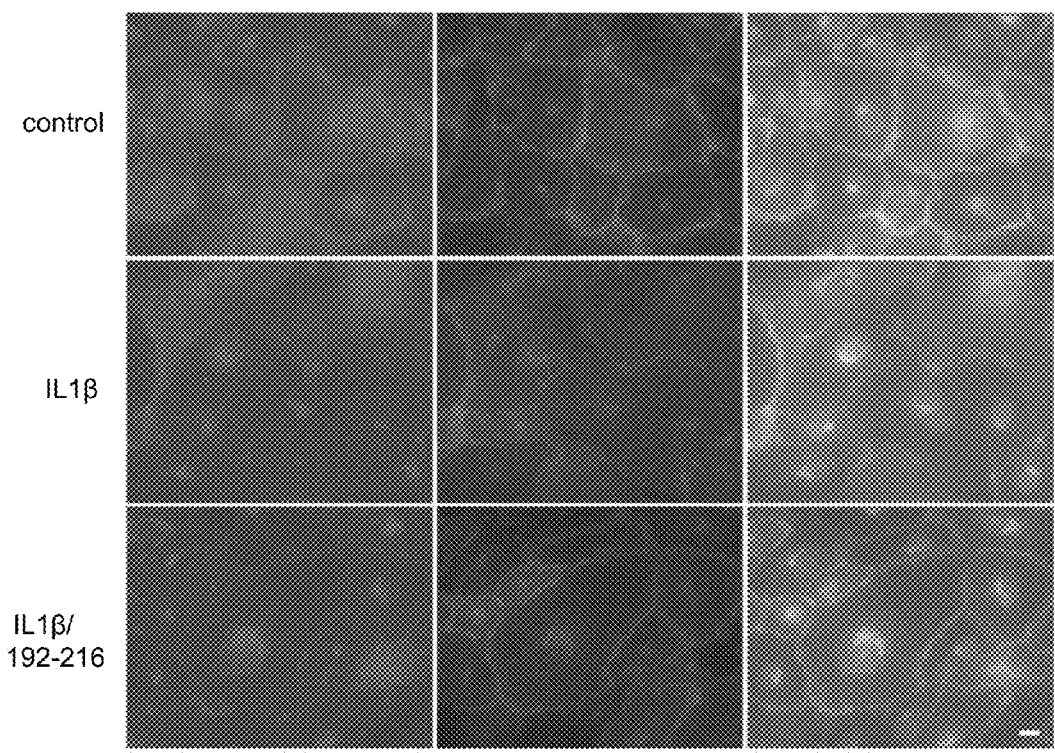
FIG. 8 includes photographs showing the results of Example 8 of the present application.

Human umbilical vein endothelial cells (HUVEC) were densely seeded on a culture dish. Interleukin 1β (IL1β) (100 ng/ml) was added to a culture medium, and the cells were then cultured at 37° C. for 24 hours. After completion of the culture, AP (negative control) or AP-F9(192-216) (1 pmol/ml) was added to the culture, and the obtained mixture was further cultured at 37° C. for 30 minutes. Thereafter, the cultured cells were fixed with 4% paraformaldehyde, and were then stained with an anti-VE cadherin antibody (green), an anti-β catenin antibody (red) or Hoechst33342 (blue), followed by performing microscopic visualization. The results are shown in FIG. 8. In the case of a sample to which AP-F9(192-216) was further added, it was confirmed that VE cadherin or β catenin was located in the intercellular adhesion portion, so that the adhesion was reinforced. The scale bar in the photograph (lower right) of FIG. 8 indicates 10 μm. In addition, in FIG. 8, the term "control" indicates the results obtained in the case of addition of AP, the term "IL1β" indicates the results obtained in the case of addition of interleukin 1β, and the term "IL1β/192-216" indicates the results obtained in the case of addition of interleukin 1β and AP-F9(192-216).

EXAMPLE 9

Figure 9:
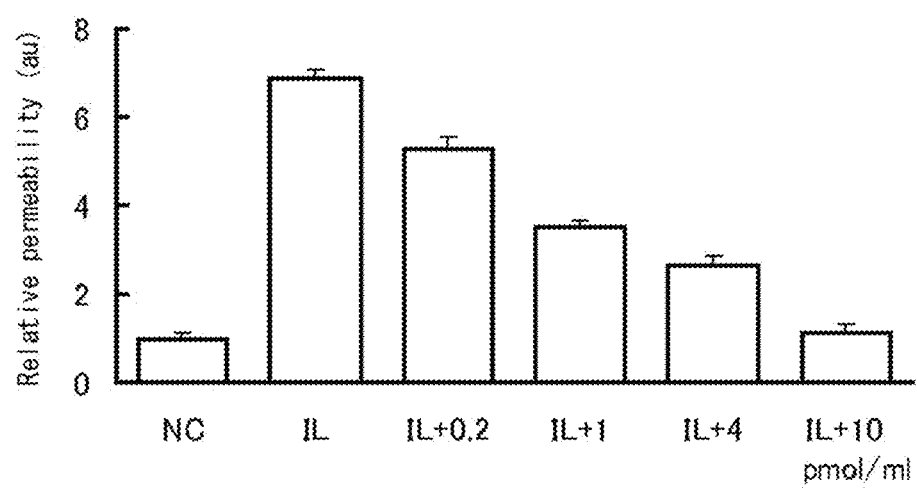
FIG. 9 is a graph showing the results of Example 9 of the present application. The numerical value of the vertical axis indicates the amount of fluorescence-modified dextran that permeated a vascular endothelial cell sheet (which is a relative amount obtained when the value of a negative control is defined as 1).

Whether or not promotion of the permeability of human umbilical vein endothelial cells (HUVEC), which is caused by interleukin 1β (IL1β) (100 ng/ml), can be suppressed by F9(192-216), was confirmed using Permeability assay kit (permeability measurement kit) manufactured by Millipore. Specific procedures were carried out according to the manual included with the kit, and the amount of fluorescence-modified dextran that permeated through a vascular endothelial cell sheet was measured (a relative amount based on the value obtained from a negative control that was set at 1). The results are shown in FIG. 9. It was confirmed that, when F9(192-216) was added in the range of additive amount that was from 0.2 pmol/ml (IL+0.2) to 10 pmol/ml (IL+10), promotion of the permeability of HUVEC was suppressed in a concentration-dependent manner. Each of the numerical values (on the vertical axis) in the graph of FIG. 9 is indicated as a mean±SD. In addition, in FIG. 9, the term "NC" indicates the results obtained in the case of addition of a negative control (in which neither IL1β nor F9(192-216) was added), the term "IL" indicates the results obtained in the case of addition of only IL1β, and the terms "IL+0.2," "IL+1," "IL+4" and "IL+10" indicate the results obtained in the case of addition of 0.2 pmol/ml, 1 pmol/ml, 4 pmol/ml and 10 pmol/ml of F9(192-216), respectively, as well as IL1β.

EXAMPLE 10

The therapeutic effects of the peptide of the present invention on model mice with pulmonary edema, which were caused by septicemia, disseminated intravascular coagulation syndrome (DIC) or acute respiratory distress syndrome (ARDS), were confirmed. It is to be noted that the term "pulmonary edema model mice" is used herein to mean mice in a state in which they were to develop pulmonary edema as a result of the administration of LPS (lipopolysaccharide; endotoxin) to normal mice, as described in Experiment 1 later.

First, as a peptide to be used in the present therapy, a peptide consisting of the following amino acid sequence (SEQ ID NO: 25), which comprised the amino acid sequence shown in SEQ ID NO: 10, was synthesized using the existing peptide synthesizer:

(SEQ ID NO: 25)
AETVFSNMDYENSTEAVFIQDDITKKKKKK.

In the above therapeutic peptide, the underlined amino acids constitute the amino acid sequence shown in SEQ ID NO: 10 (24 amino acids).

Similarly, as a peptide to be used as a control, the following peptide (SEQ ID NO: 26) was also synthesized:

(SEQ ID NO: 26)
TIDDQIFVAETSNEYDMNSFVTEAKKKKKK.

The above control peptide (SEQ ID NO: 26) was synthesized by reversely disposing the N-terminus and C-terminus of only the underlined amino acid sequence portion (SEQ ID NO: 10) in the amino acid sequence shown in SEQ ID NO: 25.

In the C-terminal side of each of the aforementioned peptides, six lysine residues are present. These lysine residues were added to each peptide, so that the solubility of the peptide as a whole could be maintained and it made possible to adjust pH.

<Experiment 1>

A comparison experiment was carried out on a normal mouse group (healthy mice), an "LPS (lipopolysaccharide; endotoxin)+control peptide (SEQ ID NO: 26)" administration group, and an "LPS+therapeutic peptide (SEQ ID NO: 25)" administration group (7 mice/each group). Specifically, LPS was dissolved in PBS, and the obtained solution was then administered to the mice at a dose of 100 µg/body weight (g) via intravenous injection. Three hours after the administration, each of the synthetic peptides (SEQ ID NOS: 25 and 26) was administered to the mice at a dose of 350 ng/body weight (g) via intravenous injection. Thereafter, the lung was removed from the mice in each group, and the weight of each lung was measured. The ratio of the weight (g) of the lung to the body weight (g) (lung weight (g)/body weight (g)) was calculated. The results are shown in FIG. 10.

Figure 10:
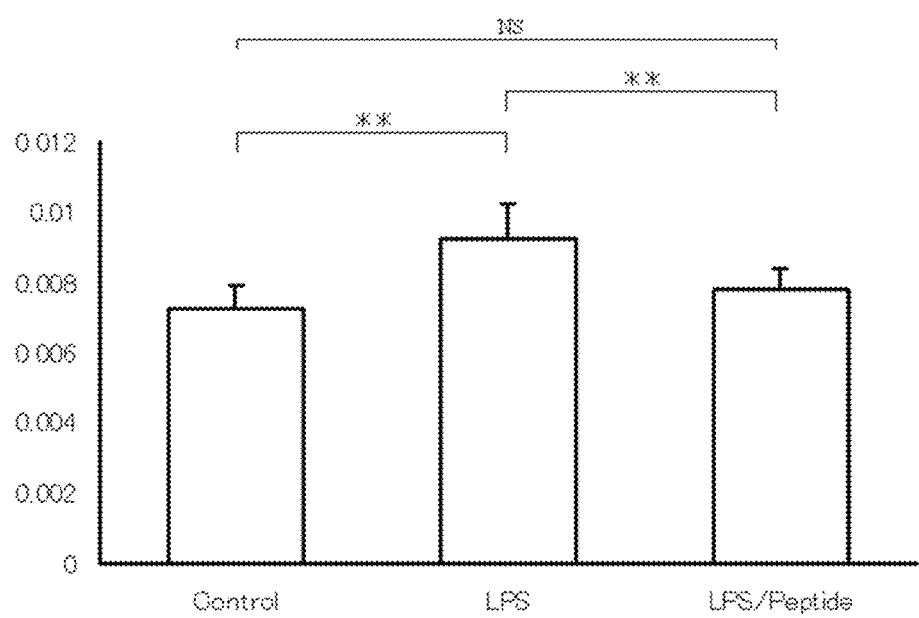
FIG. 10 is a graph showing the results of Experiment 1 in Example 10 of the present application, namely, the results regarding therapeutic effects on pulmonary edema (the effect of reducing the amount of lung water). In the graph, "Control" indicates normal mice, "LPS" indicates an "LPS (lipopolysaccharide)+control peptide (SEQ ID NO: 26)" administration group, and "LPS/Peptide" indicates an "LPS (lipopolysaccharide)+therapeutic peptide (SEQ ID NO: 25)" administration group. In addition, the numerical value of the vertical axis in the graph indicates the ratio of the weight (g) of lung to the body weight (g) of each mouse (lung weight (g)/body weight (g)).

As shown in FIG. 10, it was confirmed that the lung weight was increased by 28% by administration of LPS, but that 72% of the aforementioned increased amount could be reduced by the subsequent administration of the therapeutic peptide (SEQ ID NO: 25).

<Experiment 2>

Individual peptides used in the above Experiment 1 were administered at a dose of 350 ng/body weight (g) to normal mice (healthy mice that were not the above described pulmonary edema model mice) via intravenous injection, and the mice were then observed. As a result, it was confirmed that no particular change was found in the mice (there was no acute toxicity).

From the results of the above described Experiments 1 and 2, it was confirmed that the peptide of the present invention has in vivo therapeutic effects on pulmonary edema, and that it has no fetal acute toxicity.

INDUSTRIAL APPLICABILITY

According to the present invention, there can be provided a therapeutic agent for epithelial and endothelial injury, and in particular, a therapeutic agent for epithelial and endothelial microinjury. Also, the present invention is able to provide a spread inducer of epithelial and endothelial cells.

The aforementioned therapeutic agent and spread inducer are extremely useful in that these agents can be used for the treatment of various types of diseases or pathological conditions, which are associated with epithelial and endothelial injury (in particular, microinjury).

Sequence Listing Free Text

SEQ ID NO: 25: Synthetic peptide

SEQ ID NO: 26: Synthetic peptide

The invention claimed is:

1. A fusion protein consisting of a factor IX activation peptide or a fragment thereof and a poly-lysine peptide, said activation peptide capable of repairing epithelial and endothelial cell injury or capable of inducing the spread of epithelial and endothelial cells.

2. The fusion protein of claim 1, wherein the poly-lysine peptide consists of six lysine amino acids.

3. The fusion protein of claim 1, wherein the factor IX activation peptide is the human factor IX activation peptide consisting of SEQ ID NO: 20, or a fragment thereof.

4. The fusion protein of claim 1, wherein the factor IX activation peptide is the mouse factor IX activation peptide consisting of SEQ ID NO: 12, or a fragment thereof.

5. A pharmaceutical composition comprising the fusion protein of claim 1 and a pharmaceutically acceptable carrier.

6. A method for inducing the spread of epithelial and endothelial cells in a subject in need thereof, said method comprising administering the fusion protein of claim 1 to said subject in need thereof, wherein said epithelial and endothelial cells are induced to spread.

7. A method for treating disease or pathological conditions associated with epithelial and endothelial cell injury, said method comprising administering the fusion protein of claim 1 to said subject in need thereof, wherein said disease or pathological condition associated with epithelial and endothelial cell injury is treated.

8. The method of claim 7, wherein said epithelial and endothelial cell injury is microinjury.

9. The method of claim 7, wherein the disease or pathological conditions associated with epithelial and endothelial cell injury is at least one disease or condition selected from the group consisting of septicemia, arteriosclerosis, acute myocardial infarction, angina, artery vein thrombosis, brain edema in cerebra vascular disease, bronchial asthma, and increased vascular permeability.

* * * * *